US012157902B2

(12) United States Patent
Park et al.

(10) Patent No.: US 12,157,902 B2
(45) **Date of Patent: *Dec. 3, 2024**

(54) RECOMBINANT ACID-RESISTANT YEAST WITH SUPPRESSED GLYCEROL PRODUCTION AND METHOD OF PRODUCING LACTIC ACID USING THE SAME

(71) Applicant: SK INNOVATION CO., LTD., Seoul (KR)

(72) Inventors: Jae Yeon Park, Daejeon (KR); Ki Sung Lee, Daejeon (KR); Tae Young Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 286 days.

This patent is subject to a terminal disclaimer.

(21) Appl. No.: 17/218,971

(22) Filed: Mar. 31, 2021

(65) Prior Publication Data

US 2021/0324346 A1 Oct. 21, 2021

(30) Foreign Application Priority Data

Apr. 17, 2020 (KR) ........................ 10-2020-0046779

(51) Int. Cl.

| | |
|---|---|
| ***C12N 9/04*** | (2006.01) |
| ***C12N 1/21*** | (2006.01) |
| ***C12N 9/88*** | (2006.01) |
| ***C12P 7/56*** | (2006.01) |

(52) U.S. Cl.

CPC ............. *C12N 9/0006* (2013.01); *C12N 9/88* (2013.01); *C12P 7/56* (2013.01); *C12Y 101/01001* (2013.01); *C12Y 101/01008* (2013.01); *C12Y 101/01027* (2013.01); *C12Y 101/05003* (2013.01); *C12Y 401/01001* (2013.01)

(58) Field of Classification Search

None

See application file for complete search history.

(56) References Cited

U.S. PATENT DOCUMENTS

| | | | | |
|---|---|---|---|---|
| 7,049,108 | B2 | 5/2006 | Porro et al. | |
| 7,141,410 | B2 | 11/2006 | Rajgarhia et al. | |
| 7,232,664 | B2 | 6/2007 | Van Hoek et al. | |
| 7,534,597 | B2 | 5/2009 | Hause et al. | |
| 8,137,953 | B2 | 3/2012 | Miller et al. | |
| 9,353,388 | B2 * | 5/2016 | Kim | C07K 14/395 |
| 9,617,570 | B2 | 4/2017 | Lim et al. | |
| 9,758,770 | B2 | 9/2017 | Lim et al. | |
| 2003/0032152 | A1 | 2/2003 | Porro et al. | |
| 2003/0190630 | A1 | 10/2003 | Rajgarhia et al. | |
| 2009/0053782 | A1 | 2/2009 | Dundon et al. | |
| 2012/0058529 | A1 | 3/2012 | Ikushima et al. | |
| 2012/0214214 | A1 | 8/2012 | Hara et al. | |
| 2012/0295319 | A1 * | 11/2012 | Nevoigt | C12N 9/0006 435/254.2 |
| 2013/0071893 | A1 | 3/2013 | Lynch et al. | |
| 2015/0064752 | A1 * | 3/2015 | Lee | C12P 7/40 435/254.2 |
| 2015/0152447 | A1 | 6/2015 | Kim et al. | |
| 2016/0002678 | A1 * | 1/2016 | Song | C12N 15/81 435/143 |
| 2016/0024484 | A1 | 1/2016 | Lim et al. | |
| 2016/0333380 | A1 | 11/2016 | Chung et al. | |
| 2021/0155945 | A1 | 5/2021 | Park et al. | |
| 2021/0403882 | A1 | 12/2021 | Park et al. | |
| 2022/0049262 | A1 | 2/2022 | Park et al. | |
| 2022/0056459 | A1 | 2/2022 | Park et al. | |

FOREIGN PATENT DOCUMENTS

| | | | |
|---|---|---|---|
| CN | 106459881 | A | 2/2017 |
| EP | 2873725 | A1 | 5/2015 |
| EP | 3795689 | A1 | 3/2021 |
| EP | 3808852 | A1 | 4/2021 |
| EP | 3865577 | A2 | 8/2021 |
| JP | 2001204464 | A | 7/2001 |
| JP | 2005137306 | A | 6/2005 |
| JP | 4095889 | B2 | 6/2008 |
| JP | 4692173 | B2 | 6/2011 |
| JP | 4700395 | B2 | 6/2011 |
| JP | 201261006 | A | 3/2012 |

(Continued)

OTHER PUBLICATIONS

Pearson, Effective protein sequence comparison, Methods Enzymology 266, 1996, 227-58. (Year: 1996).*
Uniprot, Accession No. A0A1X7R452, 2019, www.uniprot.org. (Year: 2019).*
Bon et al., Genomic exploration of the Hemisacomycetous yeasts, FEBS Lett. 487, 2000, 42-46. (Year: 2000).*
GenBank, Accession No. AL409647.1, 2001, www.ncbi.nlm.nih.gov. (Year: 2001).*
Chen et al., Cloning and characterization of a NAD+-dependent glycerol-3-phosphate dehydrogenase gene from Candida glycerinogenes, FEMS Yeast Res. 8, 2008, 725-34. (Year: 2008).*
GenBank, Accession No. AL409824.1, 2001, www.ncbi.nlm.gov. (Year: 2001).*
GenBank, Accession No. AL409367.1, 2001, www.ncbi.nlm.gov. (Year: 2001).*
Ellen I. Garvie, Microbiological Reviews, 106-139, 1980.
Michael Sauer et al., Biotechnology and Genetic Engineering Reviews, 27:229-256, 2010.

(Continued)

*Primary Examiner* — Todd M Epstein

(74) *Attorney, Agent, or Firm* — The Webb Law Firm

(57) ABSTRACT

Disclosed are a recombinant acid-resistant yeast having lactic acid-producing ability and suppressed glycerol production and a method of preparing lactic acid using the same. More particularly, disclosed are a recombinant acid-resistant yeast into which a gene involved in lactic acid production is introduced and in which a gene involved in glycerol production is deleted or attenuated, and a method of preparing lactic acid using the same. When producing lactic acid using the recombinant acid-resistant yeast, the production of lactic acid is maintained while the production of glycerol is reduced, so crosslinking by glycerol can be suppressed in the oligomerization reaction for conversion to lactide, and thus the conversion yield of lactic acid to lactide can be increased.

12 Claims, 5 Drawing Sheets

Specification includes a Sequence Listing.

(56) References Cited

FOREIGN PATENT DOCUMENTS

| | | | | |
|---|---|---|---|---|
| JP | 2018518175 A | 7/2018 | | |
| KR | 101576186 B1 | 12/2015 | | |
| KR | 1020160012561 A | 2/2016 | | |
| KR | 1020160133308 A | 11/2016 | | |
| KR | 101686900 B1 | 12/2016 | | |
| KR | 1020170008151 A | 1/2017 | | |
| KR | 20170025315 A * | 3/2017 | ............ | C12N 15/81 |
| KR | 1020170077599 A | 7/2017 | | |
| KR | 1020180015591 A | 2/2018 | | |
| KR | 1020190121030 A | 10/2019 | | |
| KR | 1020190121031 A | 10/2019 | | |
| KR | 102140596 B1 | 8/2020 | | |
| KR | 1020210041903 A | 4/2021 | | |
| WO | 9914335 A1 | 3/1999 | | |
| WO | 2005052174 A3 | 6/2005 | | |
| WO | 2007117282 A2 | 10/2007 | | |
| WO | 2016056566 A1 | 7/2017 | | |
| WO | 2019203436 A1 | 10/2019 | | |
| WO | 2020075986 A2 | 4/2020 | | |

OTHER PUBLICATIONS

Roeland Costenoble et al., Microaerobic glycerol formation in *Saccharomyces cerevisiae*, Yeast 2000; 16: 1483-1495.
Elke Nevoigt and Ulf Stahl, Osmoregulation and glycerol metabolism in the yeast *Saccharomyces cerevisiae*, FEMS Microbiology Reviews 21 (1997) 231-241.
Joseph P. Dexter et al., Robust network structure of the Sln1-Ypd1-Ssk1 three-component phospho-relay prevents unintended activation of the HOG MAPK pathway in *Saccharomyces cerevisiae*, BMC Systems Biology (2015) 9:17.
Hubmann et al., Identification of multiple interacting alleles conferring low glycerol and high ethanol yield in *Saccharomyces cerevisiae* ethanolic fermentation, Biotechnology for Biofuels 2013, 6:87.
Hubmann et al. Quantitative trait analysis of yeast biodiversity yields novel gene tools for metabolic engineering, Metabolic Engineering 17 (2013) 68-81.
Jacobus Albertyn et al., GPD1, which encodes glycerol-3-phosphate dehydrogenase, is essential for growth under osmotic stress in *Saccharomyces cerevisiae*, and its expression is regulated by the high osmolarity glycerol response pathway, Molecular and cellular biology, Jun. 1994, 4135-4144.
Wen Shen et al., Effect on electrospun fibres by synthesis of high branching polylactic acid, R. Soc. open sci. 5: 180134, 2018.
Extended European Search Report Issued Sep. 16, 2021 from corresponding European Patent Application 21163490.2.
Abbott et al., "Metabolic engineering of *Saccharomyces cerevisiae* for production of carboxylic acids: current status and challenges", FEMS Yeast Research, 2009, pp. 1123-1136, vol. 9.
Baek et al., "Metabolic engineering and adaptive evolution for efficient production of D-lactic acid in *Saccharomyces cerevisiae*", Applied Microbiology and Biotechnology, 2016, pp. 2737-2748, vol. 100.
Devos et al., "Practical Limits of Function Prediction" Proteins: Structure, Function and Genetics, 2000, pp. 98-107, vol. 41.
Feldman-Salit et al., "Regulation of the activity of lactate dehydrogenases from four lactic acid bacteria" Journal of Biological Chemistry 288.29 (2013): pp. 21295-21306.
Guiard, B., "Structure, expression and regulation of a nuclear gene encoding a mitochondrial protein: the yeast L(+)-lactate cytochrome c oxidoreductase (cytochrome b2)," EMBO J., 1985, pp. 3265-3272, vol. 12.
Halestrap, A.P., The monocarboxylate transporter family—Structure and Functional Characterization, IUBMB Life, 2012, pp. 1-9, vol. 64, No. 1.
Hoppner et al., "Purification and kinetic characteristics of pyruvate decarboxylase and ethanol dehydrogenase from Zymomonas mobilis in relation to ethanol production", European Journal of Applied Microbiology and Biotechnology, 1983, pp. 152-157, vol. 17.
Ishida et al., "Efficient production of L-lactic acid by metabolically engineered *Saccharomyces cerevisiae* with a genome-integrated L-lactate dehydrogenase gene", Applied and Environmental Microbiology, 2005, pp. 1964-1970, vol. 71, No. 4.
Kisselev, L., "Polypeptide Release Factors in Prokaryotes and Eukaryotes: Same Function, Different Structure" Structure, 2002, pp. 8-9, vol. 10.
Lodi et al., "Isolation of the DLD gene of *Saccharomyces cerevisiae* encoding the mitochondrial enzyme D-lactate ferricytochrome c oxidoreductase", Mol. Gen. Genet., 1993, pp. 315-324, vol. 238.
NCBI, GenBank Accession No. SMN19920.1, similar to *Saccharomyces cerevisiae* YLR044C PDC1 Major of three pyruvate decarboxylase isozymes, key enzyme in alcoholic fermentation, decarboxylates pyruvate to acetaldehyde [Kazachstania saulgeensis], 2017.
Ookubo et al., "Improvement of L-lactate production by CYB2 gene disruption in a Recombinant *Saccharomyces cerevisiae* Strain under low pH condition", Biosci. Biotechnol. Biochem., 2008, pp. 3063-3066, vol. 72, No. 11.
Pacheco et al., Lactic Acid production in *Saccharomyces cerevisiae* is modulated by expression of the monocarxboxylate transporter Jen1 and Ady2, FEMS Yeast Res, 2012, pp. 375-381, vol. 12.
Park et al., "Low-pH production of D-lactic acid using newly isolated acid tolerant yeast *Pichia kudriavzevii* NG7", Biotechnology and Bioengineering, 2018, pp. 2232-2242, vol. 115.
Savijoki et al., "Molecular genetic characterization of the L-lactate dehydrogenase gene (ldhL) of Lactobacillus helveticus and biochemical characterization of the enzyme" Applied and Environmental Microbiology 63.7 (1997): pp. 2850-2856.
Skory et al., "Inhibition of Rhizopus lactate dehydrogenase by fructose 1,6-bisphosphate" Enzyme and Microbial Technology 44 (2009): pp. 242-247.
Skory et al., "Lactic acid production by *Saccharomyces cerevisiae* expressing a Rhizopus oryzae lactate dehydrogenase gene", Journal of Industrial Microbiology and Biotechnology, 2003, pp. 22-27, vol. 30, No. 1.
Tokuhiro et al., "Double mutation of the PDC1 and ADH1 genes improves lactate production in the yeast *Saccharomyces cerevisiae* expressing the bovine lactate dehydrogenase gene" Applied Microbiology and Biotechnology 82.5 (2009): pp. 883-890.
Valli et al., "Improvement of Lactic acid production in *Saccharomyces cerevisiae* by cell sorting for high intracellular pH", Appl Environ Microbiol, 2006, pp. 5492-5499, vol. 72, No. 8.
Van Maris et al., "Mini-review Microbial export of lactic and 3-hydroxypropanoic acid: implication for industrial fermentation processes", Metabolic Engineering, 2004, pp. 245-255, vol. 6.
Whisstock et al., "Prediction of protein function from protein sequence and structure" Quarterly Reviews of Biophysics, 2003, pp. 307-340, vol. 36, No. (3).
Witkowski et al., "Conversion of a Beta-Ketoacyl Synthase to a Malonyl Decarboxylase by Replacement of the Active-Site Cysteine with Glutamine" Biochemistry, 1999, pp. 11643-11650, vol. 38.
Zhang et al., "Adaptive mutations in sugar metabolism restore growth on glucose in a pyruvate decarboxylase negative yeast strain" Microbial Cell Factories 14.1 (2015): article 116, 11 pages.
Abbott et al., "Catalase Overexpression Reduces Lactic Acid-Induced Oxidative Stress in *Saccharomyces cerevisiae*", Applied and Environmental Microbiology, 2009, pp. 2320-2325, vol. 75, No. 8.
Fletcher et al., "Evolutionary engineering reveals divergent paths when yeast is adapted to different acidic environments", Metabolic Engineering, 2017, pp. 1-37.
Gao et al., "Zinc finger protein 637 protects cells against oxidative stress-induced premature senescence by mTERT-mediated telomerase activity and telomere maintenance", Cell Death and Disease, 2014, pp. 1-13, vol. 5, No. e1334.
GenEmbl Accession No. CP024408, 2017.
Lee et al.,"Co-expression of two heterologous lactate dehydrogenases genes in Kluyveromyces marxianus for L-lactic acid production", J. Biotechnology, 2017, pp. 81-86, vol. 241.

(56) References Cited

OTHER PUBLICATIONS

Long et al., "How adaptive evolution reshapes metabolism to improve fitness: recent advances and future outlook" Current Opinion in Chemical Engineering, 2018, pp. 209-215, vol. 22.
Prasad et al., "Molecular Mechanisms of Zinc as a Pro-Antioxidant Mediator: Clinical Therapeutic Implications", Antioxidants, 2019, pp. 1-22, vol. 8, No. 164.
Van Maris et al., "Homofermentative Lactate Production Cannot Sustain Anaerobic Growth of Engineered *Saccharomyces cerevisiae*: Possible Consequence of Energy-Dependent Lactate Export", Appl. Environ. Microbiol., 2004, pp. 2898-2905, vol. 70, No. 5.
Zhu et al., "Evolutionary engineering of industrial microorganims-strategies and applications", Applied Microbiology and Biotechnology, 2018, pp. 4615-4627.
Zhou et al., "Selective Sensitization of Zinc Finger Protein Oxidation by ROS Through Arsenic Binding", The Journal of Biological Chemistry, 2015, pp. 18361-18369, vol. 290.
Hyland, P., "Development of a Platform Strain for Production of Adipic Acid Yields Insights into the Localized Redox of Metabolism of *S. cerevisiae*", Dissertation, University of Toronto, 2013.
Jiang et al., "Progress of succinic acid production from renewable resources: metabolic and fermentative strategies", Bioresource Technology, 2017, pp. 1-38.
Karlin et al., "Applications and statistics for multiple high-scoring segments in molecular sequences", Proceedings of the National Academy of Sciences, 1993, pp. 5873-5877, vol. 90, No. 12.
Nishant et al., "The baker's yeast diploid genome is remarkably stable in vegetative growth and meiosis", PLoS Genet, 2010, pp. 1-15, vol. 6, No. 9 e1001109.
Steiger et al., "Biochemistry of microbial itaconic acid production", Frontiers in Microbiology, 2013, pp. 1-5, vol. 4, No. 23.
Storchova, Z., "Ploidy changes and genome stability in yeast", Yeast, 2014, pp. 421-430, vol. 31, No. 11.
Zhang et al., "A synthetic metabolic pathway for production of the platform chemical isobutyric acid", ChemSusChem, 2011, pp. 1068-1070, vol. 4, No. 8.
Zelle et al., "Malic acid production by *Saccharomyces cerevisiae*: engineering of pyruvate carboxylation, oxaloacetate reduction, and malate export", Applied and Environmental Microbiology, 2008, pp. 2766-2777, vol. 74, No. 9.
Kozak, "Initiation of translation in prokaryotes and eukaryotes", Gene, 1999, pp. 187-208, vol. 234.
Zhou et al., "Global analysis of gene transcription regulation in prokaryotes", Cell. Mol. Life Sci., 2006, pp. 2260-2290, vol. 63.

* cited by examiner

SEQUENCE LISTING

```
<160> NUMBER OF SEQ ID NOS: 53

<210> SEQ ID NO 1
<211> LENGTH: 1170
<212> TYPE: DNA
<213> ORGANISM: Artificial Sequence
<220> FEATURE:
<223> OTHER INFORMATION: GPD1_g1544 gene allele1_ORF

<400> SEQUENCE: 1

atggttgcta ccgatagatt aaatcaaact tctaatattt tacataaatc aatgaaaaga     60

gcttcaagta tagcgcatct aactgcttta gatcatcctt ttaaaattgc tgttatcggt    120

tccggtaact ggggtactac tatcgctaaa gtagtctctg aaaatgcagc tttaaatcca    180

caattatttg cttccgaagt aagaatgtgg gtctttgaag aaaaaattga tggtaaaaat    240

ttaacagaaa ttataaatac agatcatgaa aatgttaaat atttaccaaa tattaaatta    300

ccagtaaatt taatcgctac tccagatctt ttaaagactg tagaaggcgc agatataatc    360

attttcaata ttcctcatca attcttaact agaattgtac aacaattgaa aggtcatgtc    420

gattctcatg ttcgtgcaat ctcatgtcta aagggtttcg aagtcggtgc tagaggtgta    480

caattactat ccacttatat caccgatgaa ttaggtatcg aatgtggtgc tttatcaggt    540

gccaatatcg ctactgaagt cgctaaggaa aactggtcag aaactaccgt tgcctatcat    600

atcccagaag atttcagagg tgaaggttac gatgtagatc ataaagtatt aaaggcttta    660

ttccacagac cttatttcca cgtctctgtc attgaagatg tcgcaggtat ctctgttgcc    720

ggtgctttga aaaacgttgt cgctttaggt tgtggtttcg tcgaaggttt aggctggggt    780

aataatgctt ctgcagctat tcaaagagtc ggtcttggtg aaatcatcaa gtttggtcaa    840

atgttcttcc cagaatctcg tgtcgaaact tattatcaag aatccgcagg tgtcgcagat    900

ttaattacta cttgtgcagg tggtagaaac gttaaagttg ctaaattaat ggctgaaagt    960

ggtatgagtg ccttagatgc tgaaaagaaa ttattaaatg gtcaatctgc tcaaggtatt   1020

attacttgta aagaagttca tgaatggtta gaaacttgta attcaatttc tgaattccca   1080

ttatttgaag ccgtttatca aattatttac aataatttac caatggaaaa tatacctgat   1140

atgatcgatg aattagaagt tttccgttaa                                    1170
```

<210> SEQ ID NO 2
<211> LENGTH: 1170
<212> TYPE: DNA
<213> ORGANISM: Artificial Sequence
<220> FEATURE:
<223> OTHER INFORMATION: GPD1_g1544 gene allele2_ORF

<400> SEQUENCE: 2
atggttgcta ccgatagatt aaatcaaact tctaatattt tacataaatc aatgaaaaga 60
gcttcaagta tagcgcatct aactgcttta gatcatcctt ttaaaatcgc tgttatcggt 120
tccggtaact ggggtactac tatcgctaaa gtagtctctg aaaatgcagc tttaaatcca 180
caattatttg cttccgaagt aagaatgtgg gtctttgaag aaaaaattga tggtaaaaat 240
ttaacagaaa ttataaatac agatcatgaa aatgttaaat atttaccaaa tatcaaatta 300
ccagtaaatt taatcgctac tccagatctt ttaaagactg tcgagggtgc agatataatc 360
attttcaata ttcctcatca attcttaact agaattgtac aacaattgaa aggtcatgtc 420
gattctcatg ttcgtgcaat ctcatgtcta aagggtttcg aagtcggtgc tagaggtgta 480
caattactat ccacttatat caccgatgaa ttaggtatcg aatgtggtgc tttatcaggt 540
gctaatatcg ctactgaagt cgctaaggaa aactggtccg aaactaccgt tgcttatcat 600
atcccagaag atttcagagg tgaaggttac gatgtagatc ataaagtatt aaaggcttta 660
ttccatagac cttatttcca cgtctccgtg attgaagatg tcgcaggtat ctctgttgcc 720
ggtgctttga aaaacgttgt cgctttaggt tgtggtttcg tcgaaggttt aggctggggt 780
aataatgctt ctgcagctat tcaaagagtc ggtcttggtg aaattatcaa gtttggtcaa 840
atgttcttcc cagaatctcg tgtcgaaact tattatcaag aatccgcagg tgtcgcagat 900
ttaattacta cttgtgcagg tggtagaaac gttaaagttg ctaaattaat ggctgaaagt 960
ggtatgagtg ccttagatgc tgaaaagaaa ttattaaatg gtcaatctgc tcaaggtatt 1020
attacttgta aagaagttca tgaatggtta gaaacttgta attcaatttc tgaattccca 1080
ttatttgaag ccgtttatca aattatttac aataatttac caatggaaaa tatacctgat 1140
atgatcgatg aattagaagt tttccgttaa 1170

<210> SEQ ID NO 3
<211> LENGTH: 389
<212> TYPE: PRT
<213> ORGANISM: Artificial Sequence
<220> FEATURE:
<223> OTHER INFORMATION: GPD1(g1544)allele1/2_ORF

<400> SEQUENCE: 3

Met Val Ala Thr Asp Arg Leu Asn Gln Thr Ser Asn Ile Leu His Lys
1 5 10 15

Ser Met Lys Arg Ala Ser Ser Ile Ala His Leu Thr Ala Leu Asp His
20 25 30

Pro Phe Lys Ile Ala Val Ile Gly Ser Gly Asn Trp Gly Thr Thr Ile
35 40 45

Ala Lys Val Val Ser Glu Asn Ala Ala Leu Asn Pro Gln Leu Phe Ala
50 55 60

Ser Glu Val Arg Met Trp Val Phe Glu Glu Lys Ile Asp Gly Lys Asn
65 70 75 80

Leu Thr Glu Ile Ile Asn Thr Asp His Glu Asn Val Lys Tyr Leu Pro
85 90 95

-continued

```
Asn Ile Lys Leu Pro Val Asn Leu Ile Ala Thr Pro Asp Leu Leu Lys
            100                 105                 110

Thr Val Glu Gly Ala Asp Ile Ile Ile Phe Asn Ile Pro His Gln Phe
        115                 120                 125

Leu Thr Arg Ile Val Gln Gln Leu Lys Gly His Val Asp Ser His Val
    130                 135                 140

Arg Ala Ile Ser Cys Leu Lys Gly Phe Glu Val Gly Ala Arg Gly Val
145                 150                 155                 160

Gln Leu Leu Ser Thr Tyr Ile Thr Asp Glu Leu Gly Ile Glu Cys Gly
                165                 170                 175

Ala Leu Ser Gly Ala Asn Ile Ala Thr Glu Val Ala Lys Glu Asn Trp
            180                 185                 190

Ser Glu Thr Thr Val Ala Tyr His Ile Pro Glu Asp Phe Arg Gly Glu
        195                 200                 205

Gly Tyr Asp Val Asp His Lys Val Leu Lys Ala Leu Phe His Arg Pro
    210                 215                 220

Tyr Phe His Val Ser Val Ile Glu Asp Val Ala Gly Ile Ser Val Ala
225                 230                 235                 240

Gly Ala Leu Lys Asn Val Val Ala Leu Gly Cys Gly Phe Val Glu Gly
                245                 250                 255

Leu Gly Trp Gly Asn Asn Ala Ser Ala Ala Ile Gln Arg Val Gly Leu
            260                 265                 270

Gly Glu Ile Ile Lys Phe Gly Gln Met Phe Phe Pro Glu Ser Arg Val
        275                 280                 285

Glu Thr Tyr Tyr Gln Glu Ser Ala Gly Val Ala Asp Leu Ile Thr Thr
    290                 295                 300

Cys Ala Gly Gly Arg Asn Val Lys Val Ala Lys Leu Met Ala Glu Ser
305                 310                 315                 320

Gly Met Ser Ala Leu Asp Ala Glu Lys Lys Leu Leu Asn Gly Gln Ser
                325                 330                 335

Ala Gln Gly Ile Ile Thr Cys Lys Glu Val His Glu Trp Leu Glu Thr
            340                 345                 350

Cys Asn Ser Ile Ser Glu Phe Pro Leu Phe Glu Ala Val Tyr Gln Ile
        355                 360                 365

Ile Tyr Asn Asn Leu Pro Met Glu Asn Ile Pro Asp Met Ile Asp Glu
    370                 375                 380

Leu Glu Val Phe Arg
385
```

<210> SEQ ID NO 4
<211> LENGTH: 1328
<212> TYPE: DNA
<213> ORGANISM: Artificial Sequence
<220> FEATURE:
<223> OTHER INFORMATION: g1544 gene promoter allele1

<400> SEQUENCE: 4

```
agaaaatagt ttctccgatt aaattttttt ttcaaatcaa atctttattt aagaattggt     60

agtgtatagt agtataatat tgcctaagaa attggagtag tccgtaaaaa atgggacaaa    120

attgttgaaa ttgagcaacc tgaaaatttt atgctggtct caagtagaga aacagacgta    180

gaaccaaaat tgacccaatt tcttgttgcc tttaattggg tcattcataa gaattcaaaa    240

tattttcttt tcccactcac gcgagagata tgcgcacacg atatagttaa taccgcttgt    300

aacaatacgt agatggccaa aaatgaacaa aaggggacac tcctcaaaag aaaaaattgc    360
```

-continued

```
ttgtttggct gtcttctcca attgaaatat acacacacac cgcggtaaaa aaaaaattga    420
aatggaaatc gcggtgggac aaaagtagca accacaacaa gggaattttc cttactgctg    480
cggcagatcc ttactcatct ctcgaatata tatagcctct tgggtccacg ggcaaaaaag    540
aaataaaaaa aagagaagca acagaaccgc acgcaacgta cgcagtgatc catccatttt    600
ccacaaaatt tatctatttt cttgtctata ttttttacgt acaactaact gatcttcttg    660
tccccctccc cccatttacc cgttaaaatg aaagctgaac aacagaaaat aataattcgc    720
tctggtggac aaaaaataca agaacaagag agtatcataa ttatgtgggt cacaaatgac    780
cctacaactg tcacctagtt ggtacaaaat ttgaccctca ttctcaaata attactacat    840
ttgggtctgt attaatgcta atatttcaat atatctctat ctatcagtca catacaaatt    900
tatcttcatc ttaaagggac tcacttactc aataatggtc tatctttata tttttttcat    960
acgtatgtat gtacgtagta aagggccatc aatgatccat cttactatta ttattcttta   1020
gttatttcta agcaacaaaa ggtctgtacc acagtttcag tgtcgtcata cctcttcttt   1080
taatttcttt tcggggaggg atgtcttaat gctaacttct gtctcactat taacggtaaa   1140
tcgtattaat ctcaatatat atataaaggg ttgatatttt ccaccgtttt aaaaattatt   1200
cccttgtttc tctattatta attttagact acttatttta attatttttc ccttttttac   1260
ttattatata tatataacta tatattacca ataataatat aagcaatcac atatatttat   1320
cccattaa                                                            1328
```

```
<210> SEQ ID NO 5
<211> LENGTH: 1328
<212> TYPE: DNA
<213> ORGANISM: Artificial Sequence
<220> FEATURE:
<223> OTHER INFORMATION: g1544 gene promoter allele2

<400> SEQUENCE: 5
```

```
agaaaatagt ttctccgatt aaattttttt ttcaaatcaa atctttattt aagaattggt     60
agtgtatagt agtataaatat tgcctaagaa attggagtag tccgtaaaaa atgggacaaa   120
attgttgaaa ttgagcaacc tgaaaatttt atgctggtca caagtagaga aataggcgta    180
gaaccaaaat tgacccaatt tcttgttgcc tttaattggg tcattcataa gaattcaaaa    240
tattttcttt tcccactcac gcgagagata tgcgcacacg atataattaa taccgtttgt    300
aacaatacgt agatggccaa aaatgaacaa aatgggacac tcctcaaaag gaaaaattgc    360
ttgtttggct gtcttctcca attgaaatat acacacacac cgcggtaaaa aaaaaattga    420
aattgaaatc gcggtgggac aaaagtagca accacaacaa gggaattttc cttactgctg    480
cggcagatcc ttactcatct cttgaatata tatagcctct tgggtccacg ggcaaaaaag    540
aaaaaaaaaa aagagaagca acagaaccgc acacaacgta cgcagtgatc catccatttt    600
ccacaaaatt tatttatttt cttgtctgta ttatttacgt acaactaact gatcttcttg    660
tccccccccc cccatttacc cgttaaaatg aaagctgaac aacagaaaat aataattcgc    720
tctgatggac aaaaaataca agaacaagag agtatcatca ctatgtgggt cacaaatgac    780
cctacaactg taatctagtt gatacaaaat ttgaccctca ttctcaaata attactacat    840
ttgggtctgt attaatacta atatctgtat atctctctat ctatcagtca catacaaatt    900
tatcttcatc ttaaagggac tcacttactc aataatggtc tatctttata tttttatcat    960
acgtatgtat gtacgtagta aagggccatc aatgatccat attattatta ttattcttta   1020
gttatttcta agcaacaaaa ggtctgtacc acagtttcag tgtcgtcata tctcttattt   1080
```

taatttcttt tcggggaggg atgtcttaat gctaacttct gtctcactat taacggtaaa 1140
tcttattaat ctcaatatat atataaaggg ttgatatttt ccaacgtttt aaaacttatt 1200
cccttgtttc tatattacta atttaacatt acttatttta attatttttc cctttttttac 1260 ttattatata tatataagta catattacca ataataatat aagcaatcac atatatttat 1320
cccattaa 1328

<210> SEQ ID NO 6
<211> LENGTH: 1047
<212> TYPE: DNA
<213> ORGANISM: Artificial Sequence
<220> FEATURE:
<223> OTHER INFORMATION: ADH gene(g4423) allele1_ORF

<400> SEQUENCE: 6
atgtctattc caactactca aaagggtgtt atcttctacg aatctagagg taagctagaa 60
tacaaggaca ttccagtccc aactccaaag gctaacgaat tattaatcaa cgttaagtac 120
tctggtgttt gtcacactga tttacacgct tggcacggtg actggccatt gccagttaag 180
ctacctttag tcggtggtca cgaaggtgcc ggtgttgtcg tcgccattgg tgaatccgtt 240
aagggctgga agatcggtga ttacgccggt attaaatggt taaacggttc ttgtatgaac 300
tgtgaatact gtgaattagg taacgaatct aactgtccag aagctgattt atctggttac 360
actcacgatg gttctttcca acaatacgct accgctgatg ctatccaagc tgctaagatc 420
ccagccggta ccgatctagc cgaagttgct ccaatcttat gtgctggtgt taccgtctac 480
aaggctctaa agtccgctaa cctaagagct ggtgaatggt gtgctatctc cggtgctgct 540
ggtggtctag gttctctagc tgtccaatac gctaaggcta tgggttacag agtcgtcggt 600
attgacggtg gtgaagaaaa ggaaaagcta ttcaagtcta ttggtggtga agttttcgtc 660
gatttcacta aggaaaagga tatcattggt actattgtca aggccactaa cggtggtgct 720
cacggtgtta tcaacgtctc cgtctctgaa gccgctatcg aagcttctac caagtacgtt 780
agagctaacg gtacctccgt tttagtcggt atgccagctg gtgccgtctg tagatccgat 840
gtctttgacc acgtcgtcaa gtccatctct attgtcggtt cttacgtcgg taacagagct 900
gataccagag aagctctaga cttcttcgcc agaggtttag tcaagtctcc aatcaagatt 960
gctccattat ctgacttacc agaaattttc gaaaagatgg aaaagggtca aatcgttggt 1020
agatacgttg ttgacacttc taactaa 1047

<210> SEQ ID NO 7
<211> LENGTH: 1047
<212> TYPE: DNA
<213> ORGANISM: Artificial Sequence
<220> FEATURE:
<223> OTHER INFORMATION: ADH gene(g4423) allele2_ORF

<400> SEQUENCE: 7
atgtctattc caactactca aaagggtgtt atcttctacg aatctagagg taagctagaa 60
tacaaggaca ttccagtccc aactccaaag gctaacgaat tattaatcaa cgttaagtac 120
tctggtgttt gtcacactga tttacacgct tggcacggtg actggccatt gccagttaag 180
ctacctttag tcggtggtca cgaaggtgcc ggtgttgtcg tcgccatggg tgaatccgtt 240
aagggctgga agatcggtga ttacgccggt attaaatggt taaacggttc ttgtatgaac 300
tgtgaatact gtgaattagg taacgaatct aactgtccag aagctgattt atctggttac 360

-continued

```
actcacgatg gttctttcca acaatacgct accgctgatg ctatccaagc tgctaagatc    420

ccagccggta ccgatctagc cgaagttgcc ccaatcttat gtgctggtgt taccgtctac    480

aaggctctaa agtccgctaa cctaagagct ggtgaatggt gtgctatctc cggtgctgct    540

ggtggtctag gttctctagc tgtccaatac gctaaggcta tgggttacag agtcgtcggt    600

attgacggtg gtgatgaaaa ggaaaagcta ttcaagtcca ttggtggtga agttttcgtc    660

gatttcacta aggaaaagga tatcattggt actattgtta aggccactaa cggtggtgct    720

cacggtgtta tcaacgtctc cgtctctgaa gccgctatcg aagcttctac caagtacgtt    780

agagctaacg gtacctccgt tttagtcggt atgccagctg gtgctgtctg tagatccgat    840

gtctttgacc acgtcgtcaa gtccatctct attgtcggtt cttacgtcgg taacagagct    900

gataccagag aagctctaga cttcttcgcc agaggtttag tcaagtctcc aatcaagatt    960

gctccattat ctgacttacc agaaattttc gaaaagatgg aaaagggtca aatcattggt   1020

agatacgttg ttgacacttc taactaa                                        1047
```

```
<210> SEQ ID NO 8
<211> LENGTH: 1690
<212> TYPE: DNA
<213> ORGANISM: Artificial Sequence
<220> FEATURE:
<223> OTHER INFORMATION: PDC gene(g3002) allele1_ORF

<400> SEQUENCE: 8

atggctgaaa ttcaattagg tcgttactta ttcgaaagat taaagcaagt taaatgtact     60

accgttttcg gtttaccagg tgatttcaac ttggtcttat tagacaagtt atacgaagtc    120

gaaggtatga gatggtccgg tgacactaac gaattaaacg ctgcttacgc tgctgatggt    180

tacgctagag ttaagggtat ggccgctatg atcaccactt tcggtgtcgg tgaattatcc    240

gctttaaacg gtattgccgg ttcttactct gaacacgtcg gtgttttaca cattgtcggt    300

tgtccatcta ctttactaca agctaagggt ctattattac accacacctt agctgatggt    360

gacttcgatg tcttccacag aatgtctgct aacatctctt gtactacctc tatgatcact    420

gacattgcca ctgctccaag tgaaattgac agatgtatca gagctactta catcaaccaa    480

agaccagtct acttaggttt cccatctgac tactttgaaa agactgttcc agcttctcta    540

ttacaaactc caattgactt atctctaaag gctaacgatg ctgcttctga agatgaagtt    600

attgaagaaa tcttaaccat ggttaaggct gctaagaacc caatcatcat tgctgatgct    660

tgttcttcca gacacaacgt taaggctgaa accaagaagt tagtcgatgt taccaacttc    720

ccagccttcg ctactcctct aggtaaggcc gtcattgacg aaactcaccc aagattcggt    780

ggtatctacg ttggttctct atccagacca gctgtcaagg aagccgttga atccgctgat    840

ttaatcttat ctgtcggtgc tctattatcc gattacaaca ctgcttcttt cacttacggt    900

tacaacacca agaacattgt tgaattccac tccgaccaca tgaagatcag aaacgctacc    960

ttcccaggtg tccaaatgaa attcgttcta caaagattac taaaggtcat cggtgaagct   1020

aacaagggtt acaaggccgt tgctacccca gctaaggctc cagctaacgc tgaagtccca   1080

gcttctactc cattgaagca agaatggtta tggaacgaag tttccaactt cttccaagaa   1140

ggtgatgtta tcatcactga aaccggtact tcttccttcg gtatcaactc ctctgtcttc   1200

ccagccaaca ctattggtat ctctcaagtc ttatggggtt ccattggtta cgctggtggt   1260

gctgttgccg gtgctgcttt cgccgctgaa gaaattgacc cagctaagag agtcattcta   1320

ttcattggtg acggttctct acaattaacc gttcaagaaa tctccaccat tgttagatgg   1380
```

-continued

```
ggtctaaagc catacttatt cgtcttaaac aacgatggtt acaccattga aagattaatt   1440

cacggtccaa aggctcaata caacgaaatt caaaactggg ataacttaaa gattctacca   1500

accttcggtg ctaaggacta cgaaactcac agagttgcta ccactggtga atggaagaag   1560

ttgatcgctg acaaggcttt caacgttcca tctaagatca gaatgatcga agttatgtta   1620

ccagttatgg atggtccagc tgctttgatc gctcaaggta agctatccga agaaatgaac   1680

gctgctatgt                                                          1690
```

<210> SEQ ID NO 9
<211> LENGTH: 1689
<212> TYPE: DNA
<213> ORGANISM: Artificial Sequence
<220> FEATURE:
<223> OTHER INFORMATION: PDC gene(g3002) allele2_ORF

<400> SEQUENCE: 9

```
atggctgaag ttcaattagg tcgttactta ttcgaaagat taaagcaagt taactgtact     60

accgttttcg gtttaccagg tgatttcaac ttggtcttat tagacaagtt atacgaagtc    120

gaaggtatga gatggtccgg tgacactaac gaattaaacg ctgcttacgc tgctgatggt    180

tacgctagag ttaagggtat ggccgctatg atcaccactt tcggtgtcgg tgaattatcc    240

gctttaaacg gtattgccgg ttcttactct gaacacgtcg gtgttttaca cattgtcggt    300

tgtccatcta ctttactaca agctaagggt ctattattac accacacctt agctgatggt    360

gacttcgatg tcttccacag aatgtctgct aacatctctt gtactacctc tatgatcact    420

gacattgcca ctgctccaag tgaaattgac agatgtatca gagctactta catcaaccaa    480

agaccagtct acttaggttt cccatctgac tactttgaaa agactgttcc agcttctcta    540

ttacaaactc caattgactt atctctaaag gctaacgatg ctgcttctga agatgaagtt    600

attgaagaaa tcttaaccat ggttaaggct gctaagaacc caatcatcat tgctgatgct    660

tgttcttcca gacacaacgt taaggctgaa accaagaagt tagtcgatgt taccaacttc    720

ccagccttcg ctactcctct aggtaaggcc gtcattgacg aaactcaccc aagattcggt    780

ggtatctacg ttggttctct atccagacca gctgtcaagg aagccgttga atccgctgat    840

ttaatcttat ctgtcggtgc tctattatcc gattacaaca ctgcttcttt cacttacggt    900

tacaacacca agaacattgt tgaattccac tccgaccaca tgaagatcag aaacgctacc    960

ttcccaggtg tccaaatgaa attcgttcta caaagattac taaaggtcat cggtgaagct   1020

aacaagggtt acaaggccgt tgctacccca gctaaggctc cagctaacgc tgaagtccca   1080

gcttctactc cattgaagca agaatggtta tggaacgaag tttccaactt cttccaagaa   1140

ggtgatgtta tcatcactga aaccggtact tcttccttcg gtatcaactc ctctgtcttc   1200

ccagccaaca ctattggtat ctctcaagtc ttatggggtt ccattggtta cgctggtggt   1260

gctgttgccg gtgctgcttt cgccgctgaa gaaattgacc cagctaagag agtcattcta   1320

ttcattggtg acggttctct acaattaacc gttcaagaaa tctccaccat tgttagatgg   1380

ggtctaaagc catacttatt cgtcttaaac aacgatggtt acaccattga aagattaatt   1440

cacggtccaa aggctcaata caacgaaatt caaaactggg ataacttagc tctattacca   1500

ttattcggtg ctaaggacta cgaaactcac agagttgcta ctaccggtga atggaagaga   1560

ttagttgctg acaaggcctt caacgttcca tctaagatta gaatgattga aatcatgtta   1620

ccagttatgg acggtccagc tgctttgatt gctcaaggta agctatccga agaaatgaac   1680
```

-continued

```
gctgctatg                                                           1689


<210> SEQ ID NO 10
<211> LENGTH: 1851
<212> TYPE: DNA
<213> ORGANISM: Artificial Sequence
<220> FEATURE:
<223> OTHER INFORMATION: CYB2 gene(g2947) allele1_ORF

<400> SEQUENCE: 10

atgcaagcaa tttcaaaaaa ttcaacattt ttacgtaatt gtaaaaattt gaaatttatt      60

tcaaagaaca ttaataatag gaagttatct tcttcatcta taactttatc acaattacaa     120

tcaattaaaa ctaataccaa ttataagaat tattcttcca aaaatttacg taattcatta     180

attttattat cgtctgtatc atttttagct tattacgcta atgatcaatt acaacataat     240

actaattcat taatatctaa tgataatggt aagaatccag ctgctaataa gaaaccaatc     300

tctccagcag aagttgctaa acataacaaa ccagatgatt gttgggtagt tattgacggt     360

tacgtttacg atgtctcttt ctttattcca aatcatccag gtggtgaaga tgtcattaga     420

gctaatgcag gtaaggatgt taccgctatc ttcatgccat tacatgctaa gggtaccctt     480

gaaaagaata ttccaattga aaatcaatta ggtccattaa gtaaaccaat gcctaaaaaa     540

ttagtttgtc caccttatgc tcctggtgag acaccttatg aaattatgac taaacaaaaa     600

ttaagagata atatgccacc attaggcaca attttaaatc tttatgattt tgagagatta     660

gcttcaaaaa ttttaactaa tcaagcttgg gcttattatt cttctggtgc agatgatgaa     720

attacatata gagaaaacca taacgcttat catagaatct tttcaaaacc acatatttta     780

gtcgatgtta aggatgtcga tttgaagact actatgttag gtaataagac cgatgttcca     840

ttctatgtta gtgctactgc tttatgtaaa ttaggtaatc cagaaggtgg tgaagttgat     900

atcgctaaag gttgtggttc aacttcttat atggttcctc aaatgatttc tactttagct     960

tcttgttcat tagatgaagt cgcccagggg aaagctaacg ataaacaatt acaatggttt    1020

caattatatg ttaattccga tagaaagatt actagaaatt taattaaaca tgctgaagat    1080

ttaggtatga aggctatctt cgtcacagtt gatgctcctt ctttaggtaa tagagaaaag    1140

gatcaaaaga ttaaatttac tactcaaggt tctgagggtc caaagatttt acaaaagaaa    1200

ggtgattcct ccaatgctgc tgctgaagca aagaagaaag aaaataaatc cgatggtgcc    1260

tctaaagctt tatctaaatt tatcgatcct tctttgtcct gggaagatat cgcaaagatg    1320

agaaaattga ctaaattacc aatcgttatt aagggtgttc aaagagctga agatgctgta    1380

agagcagctc aaatgggttg tcaaggtgtt gttctttcaa atcatggtgg tagacaatta    1440

gatttctcaa gagccccaat tgaagttctt gcagagacta tgccaatttt gaaacatcat    1500

ggtctagata agaatttcga tgtctttgtc gatggtggta ttcgccgtgg tactgatatc    1560

ttaaaggcat tgtgtcttgg tgctacaggt gttggtttag gtagaccttt cttatatgct    1620

aattcttgtt atggtagaga tggtgttgct catgctattg atatcattac caaagaatta    1680

gaaatgtcta tgagattatt aggtgttagc aaaattgagg atttgaatcc aggtttctta    1740

gatttacaat ctttacatgc cagatctgtt cttgttgcta aggatgcatt atatgaaaat    1800

tcatacaagg aaccacaact agctaaattc ttaattgacg acgatgatta g             1851


<210> SEQ ID NO 11
<211> LENGTH: 1827
<212> TYPE: DNA
<213> ORGANISM: Artificial Sequence
```

<220> FEATURE:
<223> OTHER INFORMATION: CYB2 gene(g2947) allele2_ORF

<400> SEQUENCE: 11
atgcaagcaa ttaattttaa aaatttgaaa tttatttcaa agaacattaa taataggaag 60
ttatcttctt catctataac tttatcacaa ttacaatcaa ttaaaacaaa taccaattac 120
aagaattatt cttccaaaaa tttacgtaat tcattaattt tattatcttc tgtatcattt 180
ttagcttatt acgctaatga tcagttacaa cagaatacta attcattaat atctaatgaa 240
aatggtaaga atccagctgc taataagaaa ccaatctctc cagcagaagt tgctaaacat 300
aacaaaccag atgattgttg ggtagttatt gacggttacg tttacgatgt ctctttcttt 360
attccaaatc atccaggtgg tgaagatgtc attagagcta atgcaggtaa ggatgttacc 420
gctatcttca tgccattgca tgctaagggt acccttgaaa agaatattcc aattgaaaat 480
caattaggtc cattaagtaa accaatgcct aaaaaattag tttgtccacc ttatgctcct 540
ggtgagacac cttatgaaat tatgactaaa caaaaattga gagataatat gccaccatta 600
ggtacaattt taaatcttta tgattttgaa agattagctt caaaaatttt aactaatcaa 660
gcttgggctt attattcttc tggtgcagat gatgaaatta catatagaga aaaccataac 720
gcttatcata gaatcttttt caaaccacat attttagtcg atgttaagga tgtcgatttg 780
aagactacta tgttaggtaa taagaccgat gttccattct atgttagtgc tactgcttta 840
tgtaaattag gtaatccaga aggtggtgaa gttgatatcg ctaaaggttg tggttcaact 900
tcttatatgg ttcctcaaat gatttctaca ttagcttctt gttcattaga tgaagtcgcc 960
caagggaaaa ctaacgataa acaattacaa tggtttcaat tatatgttaa ttccgataga 1020
aagattacta gaaatttaat taaacatgct gaagatttag gtatgaaggc tatcttcgtc 1080
acagttgatg ctccttcttt aggtaataga gaaaaggatc aaaagattaa atttactact 1140
caaggttctg agggtccaaa gattttacaa aagaaaggtg attcctccaa tgctgctgct 1200
gaagcaaaga agaaagaaaa taaatccgat ggtgcctcta aagctttatc taaatttatc 1260
gatccttctt tgtcttggga agatatcgca aagatgagaa aattgactaa attaccaatc 1320
gttattaagg gtgttcaaag agctgaagat gctgtcagag cagctcaaat gggttgtcaa 1380
ggtgttgttc tttcaaatca tggtggtaga caattagatt tctcaagagc cccaattgaa 1440
gttcttgcag agactatgcc aattttgaaa catcatggtc tagataagaa tttcgatgtc 1500
tttgtcgatg gtggtattcg tcgtggtact gatatcttaa aggcattatg tcttggtgct 1560
acaggtgttg gtttaggtag acctttctta tatgctaatt cttgttatgg tagagatggt 1620
gttgctcatg ctattgatat cattaccaaa gaattagaaa tgtctatgag actattaggt 1680
gttagtaaaa ttgaggattt gaatccaggt ttcttagatt tacaatcttt acatgccaga 1740
tctgttcttg ttgctaagga tgcattatat gaaaattcat acaaggaacc acaactagct 1800
aaattcttaa ttgacgacga tgattag 1827

<210> SEQ ID NO 12
<211> LENGTH: 963
<212> TYPE: DNA
<213> ORGANISM: Artificial Sequence
<220> FEATURE:
<223> OTHER INFORMATION: ldh gene from Lactobacillus plantarum

<400> SEQUENCE: 12
atgtcttcta tgccaaatca tcaaaaagtt gttttggttg gtgatggtgc tgttggttct 60

-continued

```
tcttatgctt ttgctatggc tcaacaaggt attgctgaag aatttgttat tgttgatgtt    120

gttaaagata gaactaaagg tgatgctttg gatttggaag atgctcaagc ttttactgct    180

ccaaaaaaaa tttattctgg tgaatattct gattgtaaag atgctgattt ggttgttatt    240

actgctggtg ctccacaaaa accaggtgaa tctagattgg atttggttaa taaaaatttg    300

aatattttgt cttctattgt taaaccagtt gttgattctg gttttgatgg tatttttttg    360

gttgctgcta atccagttga tattttgact tatgctactt ggaaattttc tggttttcca    420

aaagaaagag ttattggttc tggtacttct ttggattctt ctagattgag agttgctttg    480

ggtaaacaat ttaatgttga tccaagatct gttgatgctt atattatggg tgaacatggt    540

gattctgaat ttgctgctta ttctactgct actattggta ctagaccagt tagagatgtt    600

gctaaagaac aaggtgtttc tgatgatgat ttggctaaat tggaagatgg tgttagaaat    660

aaagcttatg atattattaa tttgaaaggt gctacttttt atggtattgg tactgctttg    720

atgagaattt ctaaagctat tttgagagat gaaaatgctg ttttgccagt tggtgcttat    780

atggatggtc aatatggttt gaatgatatt tatattggta ctccagctat tattggtggt    840

actggtttga aacaaattat tgaatctcca ttgtctgctg atgaattgaa aaaaatgcaa    900

gattctgctg ctactttgaa aaaagttttg aatgatggtt tggctgaatt ggaaaataaa    960

taa                                                                  963
```

```
<210> SEQ ID NO 13
<211> LENGTH: 1134
<212> TYPE: DNA
<213> ORGANISM: Artificial Sequence
<220> FEATURE:
<223> OTHER INFORMATION: GPD2(g5617) gene allele1_ORF

<400> SEQUENCE: 13

atgcatcgtc aaccatttaa agtcacagtt attggttcag gtaattgggg tacaactatt     60

gcaaaagttg ttgcggagaa tacagttcaa aatcctcatt tatttaataa agatgttaat    120

atgtgggtat ttgaagaaat gattgatgga gaaaaattaa cagaaattat aaatacaaga    180

catcaaaatg ttaaatattt acctggaatt gatttaccac ataatttaat tgcaaatcca    240

tcattattag atagtgttaa aggtgcagat attcttgtat ttaatgtacc acatcaattt    300

ttacctaaaa ttgtatcaca attaaaggga catgtatcga atcaagttcg tgcaatttca    360

tgtttaaaag ggtttgaagt tggtgctaaa ggggtacaat tattatcatc atatattaaa    420

gatgaattag atattcaatg tggtgcatta tcaggtgcaa atttagcacc agaagttgca    480

aaagagcatt ggtcagagac aactgttgca tatcaattac catctgattt taaaggtgaa    540

ggatttgatg tagatcataa agtattaaag atgttatttc atagaccata tttccatgtt    600

aatgtaattg atgatgttgc aggtatttca attgcaggtg cattgaaaaa tgttgttgca    660

ttagcatgtg gttttgttga aggtttagga tggggtaata atgcagcagc agctatacaa    720

agagttggac ttggtgaaat tattaaattt ggtcaaatgt tttcccaga gagtcgtgtt     780

gaaacatatt atcaagaatc tgcaggtgtt gcagatttaa ttactacatg ttcaggtggt    840

agaaatgtta aagttgcaaa atatatgtca aagaatcatg ttgatgcatt tcaagctgag    900

aaagaattat taaatggtca atctgcacaa ggtgtaatta cttgtaaaga agttcatgaa    960

tggttatcaa catgtgaatt aacagaagat ttcccattat ttgaagcagt ttatcaaatt   1020

gtttataata atatgccaat ggaacaaatt cctgatatga ttgatgaatt agaaccattt   1080

gaagttgaag aagatgatga accgcaacaa gaacaacaac cagttactaa ctag         1134
```

-continued

<210> SEQ ID NO 14
<211> LENGTH: 1134
<212> TYPE: DNA
<213> ORGANISM: Artificial Sequence
<220> FEATURE:
<223> OTHER INFORMATION: GPD2(g5617) gene allele2_ORF

<400> SEQUENCE: 14
atgcatcgtc aaccatttaa agttacagtt attggttcag gtaattgggg tacaactatt 60
gcaaaagttg ttgcagagaa tacagttcaa aatcctcatt tatttaataa agatgttaat 120
atgtgggtat ttgaagaaat gattgatgga gaaaaattaa cagaaattat aaatacaaga 180
catcaaaatg ttaaatattt acctggaatt gatttaccac ataatttaat tgcaaatcca 240
tcattattag atagtgttaa aggtgcagat attcttgtat ttaatgtacc acatcaattt 300
ttacctaaaa ttgtatcaca attaaaggga catgtatcga atcaagttcg tgcaatttca 360
tgtttaaaag gttttgaagt tggtgctaaa ggggtacaat tattgtcatc atatattaaa 420
gatgaattag atattcaatg tggtgcatta tcaggtgcaa atttagcacc agaagttgca 480
aaagaacatt ggtcagagac aactgttgca tatcaattac catctgattt taaaggtgaa 540
ggatttgatg tagatcataa agtattaaaa atgttatttc atagaccata ttttcatgtt 600
aatgtaattg atgatgttgc aggtatttca attgcgggtg cattgaaaaa tgttgttgca 660
ttagcatgtg gttttgttga aggtttagga tggggtaata atgctgctgc agctatacaa 720
agagttggac ttggtgaaat tattaaattt ggtcaaatgt tttcccaga gagtcgtgtt 780 gaaacatatt atcaagaatc tgcaggtgtt gcagatttaa ttactacatg ttcaggtggt 840
agaaatgtta aagttgcaaa atatatgtca aagaatcatg ttgatgcatt tcaagctgag 900
aaagaattat taaatggtca atctgcacaa ggtgtaatta cttgtaaaga agttcatgaa 960
tggttatcaa catgtgaatt aacagaagat ttcccattat ttgaagcagt ttatcaaatt 1020
gtttataata atatgccaat ggaacaaatt cctgatatga ttgatgaatt agaaccattt 1080
gaagttgaag aagatgatga accgcaacaa gaacaacaac cagttactaa ctag 1134

<210> SEQ ID NO 15
<211> LENGTH: 377
<212> TYPE: PRT
<213> ORGANISM: Artificial Sequence
<220> FEATURE:
<223> OTHER INFORMATION: GPD2(g5617) gene allele1/2_ORF

<400> SEQUENCE: 15

Met His Arg Gln Pro Phe Lys Val Thr Val Ile Gly Ser Gly Asn Trp
1 5 10 15

Gly Thr Thr Ile Ala Lys Val Val Ala Glu Asn Thr Val Gln Asn Pro
20 25 30

His Leu Phe Asn Lys Asp Val Asn Met Trp Val Phe Glu Glu Met Ile
35 40 45

Asp Gly Glu Lys Leu Thr Glu Ile Ile Asn Thr Arg His Gln Asn Val
50 55 60

Lys Tyr Leu Pro Gly Ile Asp Leu Pro His Asn Leu Ile Ala Asn Pro
65 70 75 80

Ser Leu Leu Asp Ser Val Lys Gly Ala Asp Ile Leu Val Phe Asn Val
85 90 95

Pro His Gln Phe Leu Pro Lys Ile Val Ser Gln Leu Lys Gly His Val
100 105 110

-continued

```
Ser Asn Gln Val Arg Ala Ile Ser Cys Leu Lys Gly Phe Glu Val Gly
        115                 120                 125

Ala Lys Gly Val Gln Leu Leu Ser Ser Tyr Ile Lys Asp Glu Leu Asp
    130                 135                 140

Ile Gln Cys Gly Ala Leu Ser Gly Ala Asn Leu Ala Pro Glu Val Ala
145                 150                 155                 160

Lys Glu His Trp Ser Glu Thr Thr Val Ala Tyr Gln Leu Pro Ser Asp
                165                 170                 175

Phe Lys Gly Glu Gly Phe Asp Val Asp His Lys Val Leu Lys Met Leu
            180                 185                 190

Phe His Arg Pro Tyr Phe His Val Asn Val Ile Asp Asp Val Ala Gly
        195                 200                 205

Ile Ser Ile Ala Gly Ala Leu Lys Asn Val Val Ala Leu Ala Cys Gly
    210                 215                 220

Phe Val Glu Gly Leu Gly Trp Gly Asn Asn Ala Ala Ala Ala Ile Gln
225                 230                 235                 240

Arg Val Gly Leu Gly Glu Ile Ile Lys Phe Gly Gln Met Phe Phe Pro
                245                 250                 255

Glu Ser Arg Val Glu Thr Tyr Tyr Gln Glu Ser Ala Gly Val Ala Asp
            260                 265                 270

Leu Ile Thr Thr Cys Ser Gly Gly Arg Asn Val Lys Val Ala Lys Tyr
        275                 280                 285

Met Ser Lys Asn His Val Asp Ala Phe Gln Ala Glu Lys Glu Leu Leu
    290                 295                 300

Asn Gly Gln Ser Ala Gln Gly Val Ile Thr Cys Lys Glu Val His Glu
305                 310                 315                 320

Trp Leu Ser Thr Cys Glu Leu Thr Glu Asp Phe Pro Leu Phe Glu Ala
                325                 330                 335

Val Tyr Gln Ile Val Tyr Asn Asn Met Pro Met Glu Gln Ile Pro Asp
            340                 345                 350

Met Ile Asp Glu Leu Glu Pro Phe Glu Val Glu Glu Asp Asp Glu Pro
        355                 360                 365

Gln Gln Glu Gln Gln Pro Val Thr Asn
    370                 375
```

<210> SEQ ID NO 16
<211> LENGTH: 753
<212> TYPE: DNA
<213> ORGANISM: Artificial Sequence
<220> FEATURE:
<223> OTHER INFORMATION: GPP1(g4356) gene allele1_ORF

<400> SEQUENCE: 16

```
atgccactaa ctgaaaaacc actatctgtt aaagttaacg catgtctact agatgtagat      60

ggtacaatta ttatatcaca acctgcaatt gcagaaatgt ggagagattt tggtaaggat     120

aaaccttatt ttgattcaga acatgtaatt aaaatttctc atggttggag aacttatgat     180

gcaattgcaa aatttgctcc agattttgct actcatgaat ttgttgctaa attagaaggt     240

gcaattcctg aaaaatatgg gaaatttgct gttcaagtcc ctggtgctgt taaattttgt     300

aatgatatga attctttacc aaaggaaaaa tgggctgtag ctacttctgg tacatttgaa     360

atggcttctc aatggtttaa attcttaaat attaagagac ctgaaaattt tattactgct     420

tcaagtgtta aggaagggaa acccgctcct gaatgttatt taaagggtag aaatggttta     480

ggtttcccaa taaataaaca agatccaagt aaatcaaaag tatttgtatt tgaagatgct     540
```

-continued

```
cctgctggta tcgctgcagg taaagctgca ggttgtaaaa tcgtcggtat tgcaactact    600

tttgacgctg ataccttaaa ggagaaaggt tgtgatatta tcattaaaaa cttcgaatct    660

gttaaacttg gtaactacga cccagcaacc gatgaagttg aattgatttt caatgattat    720

ctttacgcta aggacgattt attgaaatgg taa                                 753
```

<210> SEQ ID NO 17
<211> LENGTH: 753
<212> TYPE: DNA
<213> ORGANISM: Artificial Sequence
<220> FEATURE:
<223> OTHER INFORMATION: GPP1(g4356) gene allele2_ORF

<400> SEQUENCE: 17

```
atgccactaa ctgaaaaacc actatctgtt aaagttaatg catgtctact agatgtagat     60

ggtacaatta ttatatcaca acctgcaatt gcagaaatgt ggagagattt tggtaaggat    120

aaaccttatt ttgattcaga gcatgtaatt aaaatttctc atggttggag aacttatgat    180

gcaattgcaa aatttgctcc agattttgct actcatgaat ttgttgctaa attagaaggt    240

gcaattcctg aaaaatatgg gaaatttgct gttcaagtcc ctggtgctgt taaattttgt    300

aatgatatga attctttacc aaaggaaaaa tgggctgttg ctacttctgg tacatttgaa    360

atggcttctc aatggtttaa attcttaaat attaaaagac ctgaaaattt tattactgct    420

tcaagtgtta aggaagggaa accagctcct gaatgttatt taaagggtag aaatggttta    480

ggtttcccaa taaataaaca agatccaagt aaatcaaaag ttttcgtatt tgaagatgct    540

cctgctggta tcgctgcagg taaagctgca ggttgtaaaa tcgtcggtat tgcaactact    600

tttgacgctg atactttaaa ggagaaaggt tgtgatatta tcattaaaaa cttcgaatct    660

gttaaacttg gtaactacga tccagcaact gatgaagttg aattgatttt caatgattat    720

ctttacgcta aggacgattt attgaaatgg taa                                 753
```

<210> SEQ ID NO 18
<211> LENGTH: 250
<212> TYPE: PRT
<213> ORGANISM: Artificial Sequence
<220> FEATURE:
<223> OTHER INFORMATION: GPP1(g4356) gene allele1/2_ORF

<400> SEQUENCE: 18

```
Met Pro Leu Thr Glu Lys Pro Leu Ser Val Lys Val Asn Ala Cys Leu
1               5                   10                  15

Leu Asp Val Asp Gly Thr Ile Ile Ile Ser Gln Pro Ala Ile Ala Glu
            20                  25                  30

Met Trp Arg Asp Phe Gly Lys Asp Lys Pro Tyr Phe Asp Ser Glu His
        35                  40                  45

Val Ile Lys Ile Ser His Gly Trp Arg Thr Tyr Asp Ala Ile Ala Lys
    50                  55                  60

Phe Ala Pro Asp Phe Ala Thr His Glu Phe Val Ala Lys Leu Glu Gly
65                  70                  75                  80

Ala Ile Pro Glu Lys Tyr Gly Lys Phe Ala Val Gln Val Pro Gly Ala
                85                  90                  95

Val Lys Phe Cys Asn Asp Met Asn Ser Leu Pro Lys Glu Lys Trp Ala
            100                 105                 110

Val Ala Thr Ser Gly Thr Phe Glu Met Ala Ser Gln Trp Phe Lys Phe
        115                 120                 125
```

-continued

```
Leu Asn Ile Lys Arg Pro Glu Asn Phe Ile Thr Ala Ser Ser Val Lys
    130                 135                 140

Glu Gly Lys Pro Ala Pro Glu Cys Tyr Leu Lys Gly Arg Asn Gly Leu
145                 150                 155                 160

Gly Phe Pro Ile Asn Lys Gln Asp Pro Ser Lys Ser Lys Val Phe Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Ala Asp Thr Leu Lys Glu
        195                 200                 205

Lys Gly Cys Asp Ile Ile Ile Lys Asn Phe Glu Ser Val Lys Leu Gly
    210                 215                 220

Asn Tyr Asp Pro Ala Thr Asp Glu Val Glu Leu Ile Phe Asn Asp Tyr
225                 230                 235                 240

Leu Tyr Ala Lys Asp Asp Leu Leu Lys Trp
                245                 250
```

<210> SEQ ID NO 19
<211> LENGTH: 753
<212> TYPE: DNA
<213> ORGANISM: Artificial Sequence
<220> FEATURE:
<223> OTHER INFORMATION: GPP1(g5443) gene allele1_ORF

<400> SEQUENCE: 19

```
atgcctctaa ctgaaaaacc tctatctcta aaaatcaacg ccgctttatt cgatgttgat     60

ggtaccatta tcatctctca accagctatt gctgctatgt ggagagattt cggtaaggac    120

aagccatact tcgatgctga acatgttatt cacatctctc acggttggag aaccttcgat    180

gccatcgcta aatttgctcc agatttcgct gatgaaaaat tcgttgctga attagaaggt    240

tccattccag ataaattcgg tgaacattcc atcgaagttc caggtgccgt caagttatgc    300

ggtgatctaa acaagctacc aaaggaaaag tgggctgttg ccacttctgg tacttgggaa    360

atggctcaca aatggttcga tatcctaggt attaaaagac catctaactt cattaccgcc    420

ggtgatgtta agaacggtaa gccacatcca gaaccataca ccaagggtag aaacggtcta    480

ggttacccag ttaacgaaca agacccatct aaatccaagg ttgttgtctt tgaagatgct    540

ccagctggta ttgctgccgg taaggctgct ggttgtaaga ttgttggtat tgctaccact    600

ttcgatctag atttcttaat tgaaaagggt tgtgatatca ttgtcaagaa ccacgaatct    660

attaaggttg gtggttacga tccagttact gatgaagtcg aattaatctt caccgattac    720

ttatatgcta aggatgattt actaaaatgg taa                                 753
```

<210> SEQ ID NO 20
<211> LENGTH: 753
<212> TYPE: DNA
<213> ORGANISM: Artificial Sequence
<220> FEATURE:
<223> OTHER INFORMATION: GPP1(g5443) gene allele2_ORF

<400> SEQUENCE: 20

```
atgcctctaa ctgaaaaacc tctatctcta aaaatcaacg ccgctttatt cgatgttgat     60

ggtaccatta tcatctctca accagctatt gctgctatgt ggagagattt cggtaaggac    120

aagccatact tcgatgctga acatgttatt cacatctctc acggttggag aaccttcgat    180

gccatcgcta aatttgctcc agatttcgct gatgaaaaat tcgttgctga attagaaggt    240

tccattccag ataaattcgg tgaacattcc atcgaagttc caggtgccgt caagttatgc    300
```

ggtgatctaa acaagctacc aaaggaaaag tgggctgttg ccacttctgg tacttgggaa 360
atggctcaca aatggttcga tatcctaggt attaaaagac catctaactt cattaccgcc 420
ggtgatgtta agaacggtaa gccacatcca gaaccataca ccaagggtag aaacggtcta 480
ggttacccag ttaacgaaca agacccatct aaatccaagg ttgttgtctt tgaagatgct 540
ccagctggta ttgctgccgg taaggctgct ggttgtaaga ttgttggtat tgctaccact 600
ttcgatctag atttcttaat tgaaaagggt tgtgatatca ttgtcaagaa ccacgaatct 660
attaaggttg gtggttacga tccagttact gatgaagtcg aattaatctt caccgattac 720
ttatatgcta aggatgattt actaaaatgg taa 753

<210> SEQ ID NO 21
<211> LENGTH: 250
<212> TYPE: PRT
<213> ORGANISM: Artificial Sequence
<220> FEATURE:
<223> OTHER INFORMATION: GPP1(g5443) gene allele1/2_ORF

<400> SEQUENCE: 21

Met Pro Leu Thr Glu Lys Pro Leu Ser Leu Lys Ile Asn Ala Ala Leu
1               5                   10                  15

Phe Asp Val Asp Gly Thr Ile Ile Ile Ser Gln Pro Ala Ile Ala Ala
            20                  25                  30

Met Trp Arg Asp Phe Gly Lys Asp Lys Pro Tyr Phe Asp Ala Glu His
        35                  40                  45

Val Ile His Ile Ser His Gly Trp Arg Thr Phe Asp Ala Ile Ala Lys
    50                  55                  60

Phe Ala Pro Asp Phe Ala Asp Glu Lys Phe Val Ala Glu Leu Glu Gly
65                  70                  75                  80

Ser Ile Pro Asp Lys Phe Gly Glu His Ser Ile Glu Val Pro Gly Ala
                85                  90                  95

Val Lys Leu Cys Gly Asp Leu Asn Lys Leu Pro Lys Glu Lys Trp Ala
            100                 105                 110

Val Ala Thr Ser Gly Thr Trp Glu Met Ala His Lys Trp Phe Asp Ile
        115                 120                 125

Leu Gly Ile Lys Arg Pro Ser Asn Phe Ile Thr Ala Gly Asp Val Lys
    130                 135                 140

Asn Gly Lys Pro His Pro Glu Pro Tyr Thr Lys Gly Arg Asn Gly Leu
145                 150                 155                 160

Gly Tyr Pro Val Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Ile Glu
        195                 200                 205

Lys Gly Cys Asp Ile Ile Val Lys Asn His Glu Ser Ile Lys Val Gly
    210                 215                 220

Gly Tyr Asp Pro Val Thr Asp Glu Val Glu Leu Ile Phe Thr Asp Tyr
225                 230                 235                 240

Leu Tyr Ala Lys Asp Asp Leu Leu Lys Trp
                245                 250

<210> SEQ ID NO 22
<211> LENGTH: 20
<212> TYPE: DNA

-continued

<213> ORGANISM: Artificial Sequence
<220> FEATURE:
<223> OTHER INFORMATION: primer

<400> SEQUENCE: 22
ctttgagtgc aagtatcgcc 20

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
tgtgtaattg ttcaccaaag cc 22

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gtcgattctc atgttcgtgc 20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cttagcgact tcagtagcga 20

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
catgtatcga atcaagttcg tg 22

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
caacttctgg tgctaaattt gc 22

<210> SEQ ID NO 28
<211> LENGTH: 988
<212> TYPE: DNA
<213> ORGANISM: Artificial Sequence
<220> FEATURE:
<223> OTHER INFORMATION: 5' UTR of g4423 allele 1

<400> SEQUENCE: 28
gttaactcag ttttctctct ttccctccac cccacgttac tctgcgaaca aaaatacgca 60

```
cagaatgaac atctgattga ttaatattta tatattactt agtggcaccc ctacaaacaa    120
accaatttg aatatttctc accatcatga tatttattta gggcaagaat ttcatgtaca     180
tacgtgcgtg tactgcatag ttttgttata tgtaaataac cagcaatata tcaccaatga    240
taaatgctca gtaatttatt tggaaccaaa atagtttcag taatcaaata atacaataac    300
taacaagtgc tgattataca acagctgtta acaacacaaa cacgctctct tctattctct    360
tccctgcttg ttcgtgtggt atattcccga atttgcaatt tagaaattat attttttaaa    420
agaattgttc tccatttct ggtagtcgta agtggcaaat tggatcataa gacacaatct     480
tgttagttcg actgctaaca ccagacaaga ccgaacgaaa acagaaaaaa aagataattt    540
tgttattctg ttcaattctc tctctctttt taaggtatct ttacattaca ttacatatcc    600
caaattacaa caagagcaag aaatgaagca caacaacacg ccatctttcg tgattatttt    660
atcatttcta tatcgtaact aaattaacaa atgctatgtt tcttaatttt taatgataaa    720
tctaactgct accttaattt ctcatggaaa gtggcaaata cagaaattat atattcttat    780
tcattttctt ataattttta tcaattacca aatatatata aatgcaatta attgattgtt    840
cctgtcacat aattttttt gtttgttacc tttattcttt atccatttag tttagttctt     900
atatctttct tttctatttc tctttttcgt ttaatctcac cgtacacata tatatccata    960
tatcaataca aataaaaatc atttaaaa                                       988
```

<210> SEQ ID NO 29
<211> LENGTH: 961
<212> TYPE: DNA
<213> ORGANISM: Artificial Sequence
<220> FEATURE:
<223> OTHER INFORMATION: 5' UTR of g4423 allele 2

<400> SEQUENCE: 29

```
gttaactcag ttttctctct ttccctccac cccacgttac tctgcgaaca aaaaatacgc     60
acagaatgaa catctgattg attaatattt atatattact cagtggcacc cctacaaaca    120
aaccaatttt gaatattgtt caccatcatg atatttattt agggcaagaa tttcatgtac    180
atacgtgcgt gtactgcata gttttgttat atgaaaataa ccagcaatat atcaccaatg    240
aataaattct caataattta tttggaacca aataatgcaa taactagcaa actaagtggt    300
gattatacaa cagctgttaa caacacaaac atacgctctc ttctattatc tcttccctgc    360
ttgttcgtgt ggtatattca cgaatttgca atttagaaat tatatttttt aaaagaattg    420
ttctccattt tctggtagtc gtaagtggca aattggatca taagacacaa tcttgttagt    480
tcgactgcta acaccagaca acaccgaacg aaaacaagaa aaaataatta ttctctctct    540
ttttaaggta tcttacatta catatcccaa attacaacaa gagcaagaaa tgaggcacaa    600
caacacacca tcatctttcg tgattatttt tatcatttct atcatgtaat taaattaaca    660
aatgttaagt ttattaattt ttaatgataa atctagttgc taccttaatt tctcatggaa    720
agtggcaaat actgaaatta tttaattcta ctttcatttt cttataattt ttatcaatta    780
ccaaatatat ataaatgcaa ttaattgatt gttcctgtca cataattttt tttgtttgtt    840
acctttattc tttatccatt taatttattt cttgtatctt tcttttctat ttctcttttc    900
tgtttaatct caccgtacac atatatatcc atatatcaat acaaataaaa atcatttaaa    960
a                                                                    961
```

<210> SEQ ID NO 30

-continued

<211> LENGTH: 256
<212> TYPE: DNA
<213> ORGANISM: Artificial Sequence
<220> FEATURE:
<223> OTHER INFORMATION: 3' UTR of g4423 allele 1

<400> SEQUENCE: 30
taagtcattt aatttattct tttagaatat atttattttg tctttatttt tgaaatgtta 60
atagtctttt ttttttactt tgaacaaaaa aaagtaaaat taaaacttat cttatatacg 120
cttttaaaca ttaaactcgt taacgaatta tataatgatt ttatcgaact actttatgtt 180
tttttaatag aataatcttc tttattaata taacttacta cttcttaatc ttgttgtcct 240
ccattcgaaa ctcgag 256

<210> SEQ ID NO 31
<211> LENGTH: 255
<212> TYPE: DNA
<213> ORGANISM: Artificial Sequence
<220> FEATURE:
<223> OTHER INFORMATION: 3' UTR of g4423 allele 2

<400> SEQUENCE: 31
taagtcattt aatttattct tttagaatat atttattttg tctttatttt tgaaatgtta 60
atagtctttt ttttactttg aaaaaaaaaa aaagtaaaat taaacttatc ttatatacgc 120
ttttaaacat taaactcgtt aacgaattat ataatgattt tatcgaacta ctttatgttt 180
ttttaataga ataatcttct ttattaatat aacttactac ttcttaatct tgttgtcctc 240
cattcgaaac tcgag 255

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
gcaggatatc agttgtttg 19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
aataccttgt tgagccatag 20

<210> SEQ ID NO 34
<211> LENGTH: 375
<212> TYPE: DNA
<213> ORGANISM: Artificial Sequence
<220> FEATURE:
<223> OTHER INFORMATION: 5' UTR of g2947 allele 1

<400> SEQUENCE: 34
atatattttg gctgacattg taattagatg agatccacaa tttttctttt gtttgactgt 60
tcgatatgga gaaggtggga tgcactatta ttatattcag aagtttattt gtacagttta 120
aagaacaaat agtggctaat cctatcctcg gactaaaaaa aatcgttcac ttctatccta 180
ctgtaaatct tatgaaaatg atgtaattca tatagttact atattttctt tcttttagaa 240
actttatgat atatatatat atataaaagg actaatcacc caactctcaa attcattaaa 300
aagaaatatg tttctatcat cttcttttct tattatacct cgtctaataa taaaaccaaa 360
caattttctg taaag 375

<210> SEQ ID NO 35
<211> LENGTH: 375
<212> TYPE: DNA
<213> ORGANISM: Artificial Sequence
<220> FEATURE:
<223> OTHER INFORMATION: 5' UTR of g2947 allele 2

<400> SEQUENCE: 35 atatatttg gctgacattg taattagatg agatccacaa tttttctttt gtttgactgt 60
tcgatatgga gaaggtggga tgcactatta ttatattcag aagtttattt gtacagcttg 120
aagaacaaat agtggctaat cctatcctcg gactaaaaaa aattgttcac ttttatccta 180
ctgtaaatct tatgaaaatg atgtaattca tatagttact atattttctt tcttttagaa 240
acttcatgat atatatatat atataaaagg actaatcacc caactctcaa atttattaaa 300
aagaaatatg tttctatcat cttcttttct tattatacct tctctaataa taaaaataaa 360
caactttctg taaag 375

<210> SEQ ID NO 36
<211> LENGTH: 997
<212> TYPE: DNA
<213> ORGANISM: Artificial Sequence
<220> FEATURE:
<223> OTHER INFORMATION: 3' UTR of g2947 allele 1

<400> SEQUENCE: 36
ttgtgactct atggagttta cctattttat ataccactat atcacaaaaa gtaataacaa 60
cttttcaaat ataatacaat attcaataaa tatatttata tattctaaaa tctacgtttt 120
tctctttctt aaaaaaataa acaaactgac cctttcaatc ttcaatgtga tactttactt 180
attttatttc attacacaga aaggtataaa tatatacata acttaatggt ttattcattt 240
cttcttatta gacaacgtgg ttagttgttg tttaacccat tccaataata aatcagtttg 300
taaataacct tcactgttaa atactttatt aatctctaat gaactagtta aagttttctt 360
cttattatct atcaaagtca tattgtaaat tggtttattt tcttcaaatt ctgtctttaa 420
tttaattatt tcagtaccat tcttaccact atatacgata gatttttcaa catatttctt 480
aaagaaccaa aatattacag atagtacaaa atatgtaccg actaaaattt gttgatattt 540
aacgatatta tcatgaacaa attttttatc aatgatgaaa ctgattgctg caacgatggc 600
agttgaataa ccaattaata atttctgatc aactaattca aaggtttctt catagcctaa 660
tcttttcatg acatcaggta gactttcatt tatagtttgt gatacttcag agatggaata 720
aacgttaacg ggcttactca ttgtgcttta aaggagaatg cggaattaat gagctcttta 780
ctatgtatca gaactcgaac taatgcaaag acaaatggaa taaactagtt acaatatata 840
tgaattttgt ctgttctttt ataatatatt ataatggatt tcccaaattg atgattattg 900
gttcactaag aaagctagaa agaagatgag atttctcgaa tagtaaaata ttacgttaac 960
atatctgaga ttaaaccgat agtcaatttg tacgtta 997

<210> SEQ ID NO 37
<211> LENGTH: 997
<212> TYPE: DNA

-continued

<213> ORGANISM: Artificial Sequence
<220> FEATURE:
<223> OTHER INFORMATION: 3' UTR of g2947 allele 2

<400> SEQUENCE: 37
ttgtgactct atggagttta cctattttat ataccactgt atcacaaaaa gtaataacaa 60
cttctcaaat ataatacaat atttaataaa tatatttata tattctaaaa tctacgtttt 120
tctctttctt aaaaaaataa acaaactgac cctttcaatc ttcaatgtga tactttactt 180
attttatttc attacacaga aaggtataaa tatatacata acttaatggt ttattcattt 240
cttcttatta gacagagtgg ttagttgttg tttaacccat tccaataata aatcagtttg 300
taaataacct tcactgttaa atactttatt aatctctaat gaactagtta aagttttctt 360
cttattatct atcaaagtca tattgtaaat tggtttattt tcttcaaatt ctgtctttaa 420
tttaattatt tcagtaccat tcttaccact atatacgata gatttttcaa catatttctt 480
aaagaaccaa aatattacag atagtacaaa atatgtaccg actaaaattt gttgatattt 540
aacgatatta tcatgaacaa attttttatc aatgatgaaa ctgattgctg caacgatggc 600
agttgaataa ccaattaata atttctgatc aactaattca aaggtttctt cataacctaa 660
tcttttcata acatcaggta gactttcatt tatagtttgt gatacttcag agatggaata 720
aacgttaaca ggtttactca ttgtgcttta aaggagaatg cggaattaat gagctcttta 780
ctatgtatca gaactcgaac taatgcaaag aaaaatggaa taaacttgtt acaatatgta 840
tgaattttgt ctattctttt ataataaatt ataatagatt tcccaaattg atgattattg 900
gttcactaag aaagctagaa agaagatgag atttctcgaa tagtaaaata ttaccttaac 960
atatctgaga ttaaaccgat agtcaatttg tacgtta 997

<210> SEQ ID NO 38
<211> LENGTH: 1328
<212> TYPE: DNA
<213> ORGANISM: Artificial Sequence
<220> FEATURE:
<223> OTHER INFORMATION: 5' UTR of g1544 allele 1

<400> SEQUENCE: 38
agaaaatagt ttctccgatt aaattttttt ttcaaatcaa atctttattt aagaattggt 60
agtgtatagt agtataatat tgcctaagaa attggagtag tccgtaaaaa atgggacaaa 120
attgttgaaa ttgagcaacc tgaaaatttt atgctggtct caagtagaga aacagacgta 180
gaaccaaaat tgacccaatt tcttgttgcc tttaattggg tcattcataa gaattcaaaa 240
tattttcttt tcccactcac gcgagagata tgcgcacacg atatagttaa taccgcttgt 300
aacaatacgt agatggccaa aaatgaacaa aaggggacac tcctcaaaag aaaaaattgc 360
ttgtttggct gtcttctcca attgaaatat acacacacac cgcggtaaaa aaaaaattga 420
aatggaaatc gcggtgggac aaaagtagca accacaacaa gggaattttc cttactgctg 480
cggcagatcc ttactcatct ctcgaatata tatagcctct tgggtccacg ggcaaaaaag 540
aaataaaaaa aagagaagca acagaaccgc acgcaacgta cgcagtgatc catccatttt 600
ccacaaaatt tatctatttt cttgtctata ttttttacgt acaactaact gatcttcttg 660
tccccctccc cccatttacc cgttaaaatg aaagctgaac aacagaaaat aataattcgc 720
tctggtggac aaaaaataca agaacaagag agtatcataa ttatgtgggt cacaaatgac 780
cctacaactg tcacctagtt ggtacaaaat ttgaccctca ttctcaaata attactacat 840
ttgggtctgt attaatgcta atatttcaat atatctctat ctatcagtca catacaaatt 900

-continued

```
tatcttcatc ttaaagggac tcacttactc aataatggtc tatctttata ttttttttcat     960

acgtatgtat gtacgtagta aagggccatc aatgatccat cttactatta ttattcttta    1020

gttatttcta agcaacaaaa ggtctgtacc acagtttcag tgtcgtcata cctcttcttt    1080

taatttcttt tcggggaggg atgtcttaat gctaacttct gtctcactat taacggtaaa    1140

tcgtattaat ctcaatatat atataaaggg ttgatatttt ccaccgtttt aaaaattatt    1200

cccttgtttc tctattatta attttagact acttatttta attatttttc cctttttttac   1260

ttattatata tatataacta tatattacca ataataatat aagcaatcac atatatttat    1320

cccattaa                                                             1328
```

<210> SEQ ID NO 39
<211> LENGTH: 1328
<212> TYPE: DNA
<213> ORGANISM: Artificial Sequence
<220> FEATURE:
<223> OTHER INFORMATION: 5' UTR of g1544 allele 2

<400> SEQUENCE: 39

```
agaaaatagt ttctccgatt aaattttttt ttcaaatcaa atctttattt aagaattggt      60

agtgtatagt agtataatat tgcctaagaa attggagtag tccgtaaaaa atgggacaaa     120

attgttgaaa ttgagcaacc tgaaaatttt atgctggtca caagtagaga aataggcgta     180

gaaccaaaat tgacccaatt tcttgttgcc tttaattggg tcattcataa gaattcaaaa     240

tattttcttt tcccactcac gcgagagata tgcgcacacg atataattaa taccgtttgt     300

aacaatacgt agatggccaa aaatgaacaa aatgggacac tcctcaaaag gaaaaattgc     360

ttgtttggct gtcttctcca attgaaatat acacacacac cgcggtaaaa aaaaaattga     420

aattgaaatc gcggtgggac aaaagtagca accacaacaa gggaattttc cttactgctg     480

cggcagatcc ttactcatct cttgaatata tatagcctct tgggtccacg ggcaaaaaag     540

aaaaaaaaaa aagagaagca acagaaccgc acacaacgta cgcagtgatc catccatttt     600

ccacaaaatt tatttatttt cttgtctgta ttatttacgt acaactaact gatcttcttg     660

tccccccccc cccatttacc cgttaaaatg aaagctgaac aacagaaaat aataattcgc     720

tctgatggac aaaaaataca agaacaagag agtatcatca ctatgtgggt cacaaatgac     780

cctacaactg taatctagtt gatacaaaat ttgaccctca ttctcaaata attactacat     840

ttgggtctgt attaatacta atatctgtat atctctctat ctatcagtca catacaaatt     900

tatcttcatc ttaaagggac tcacttactc aataatggtc tatctttata tttttatcat     960

acgtatgtat gtacgtagta aagggccatc aatgatccat attattatta ttattcttta    1020

gttatttcta agcaacaaaa ggtctgtacc acagtttcag tgtcgtcata tctcttattt    1080

taatttcttt tcggggaggg atgtcttaat gctaacttct gtctcactat taacggtaaa    1140

tcttattaat ctcaatatat atataaaggg ttgatatttt ccaacgtttt aaaacttatt    1200

cccttgtttc tatattacta atttaacatt acttatttta attatttttc cctttttttac   1260

ttattatata tatataagta catattacca ataataatat aagcaatcac atatatttat    1320

cccattaa                                                             1328
```

<210> SEQ ID NO 40
<211> LENGTH: 402
<212> TYPE: DNA
<213> ORGANISM: Artificial Sequence
<220> FEATURE:

<223> OTHER INFORMATION: 3' UTR of g1544 allele 1

<400> SEQUENCE: 40
tccatcatca agaatatata tatataataa agccatccct tttacgaacc tgcctgcatt 60
tgcttaagac cgagcaaaaa aaataaatta caacataacg aaaaaaacaa acaaacttaa 120
gggggagaaa aaaaaataat atcccataac ttacatacac aacatacata aaattaaaaa 180
aataaacatt ttatcaataa ttttttttta aagtatatag agctactaat attatagaaa 240
tacagacgca acttaaagaa ctttgttcaa tcttttcaat cttctcagtc ttttctagtc 300
ataataaatt atcaaatgcg aatatttaaa tcaaaattat ataaggggta tatcgtatat 360
atataaattt atcaaatgtg tatatgtatt ttattatgtt ta 402

<210> SEQ ID NO 41
<211> LENGTH: 402
<212> TYPE: DNA
<213> ORGANISM: Artificial Sequence
<220> FEATURE:
<223> OTHER INFORMATION: 3' UTR of g1544 allele 2

<400> SEQUENCE: 41
tccatcatca aaaatatata tatataataa agccatccct tttacgaacc tgcctgcatt 60
tgcttaagac cgagcaaaaa aaataaatta caatataacg aaaaaaacaa acaaacttaa 120
gggggagaaa aaaaaataat atcccataac ttacatacac aacatacata aaattaaaaa 180
aataaacatt ttatcaataa ttttttttta aagtatatat agctactaat attatagaaa 240
tacaaatgca acttaaagaa ctttgttcaa tcttttcaat cttctcaatc ttttctagtc 300
ataataaatt atcaaatgcg aatatttaaa ttaaaattat ataaagggta tatcatatat 360
atataaattt atcaattgtg tatatgtatt ttattatgtt ta 402

<210> SEQ ID NO 42
<211> LENGTH: 18
<212> TYPE: DNA
<213> ORGANISM: Artificial Sequence
<220> FEATURE:
<223> OTHER INFORMATION: primer

<400> SEQUENCE: 42
gggtactact atcgctaa 18

<210> SEQ ID NO 43
<211> LENGTH: 18
<212> TYPE: DNA
<213> ORGANISM: Artificial Sequence
<220> FEATURE:
<223> OTHER INFORMATION: primer

<400> SEQUENCE: 43
caccggcaac agagatac 18

<210> SEQ ID NO 44
<211> LENGTH: 18
<212> TYPE: DNA
<213> ORGANISM: Artificial Sequence
<220> FEATURE:
<223> OTHER INFORMATION: primer

<400> SEQUENCE: 44
cgtacgcagt gatccatc 18

<210> SEQ ID NO 45
<211> LENGTH: 18
<212> TYPE: DNA
<213> ORGANISM: Artificial Sequence
<220> FEATURE:
<223> OTHER INFORMATION: primer

<400> SEQUENCE: 45
caccggcaac agagatac 18

<210> SEQ ID NO 46
<211> LENGTH: 18
<212> TYPE: DNA
<213> ORGANISM: Artificial Sequence
<220> FEATURE:
<223> OTHER INFORMATION: primer

<400> SEQUENCE: 46
cgtacgcagt gatccatc 18

<210> SEQ ID NO 47
<211> LENGTH: 18
<212> TYPE: DNA
<213> ORGANISM: Artificial Sequence
<220> FEATURE:
<223> OTHER INFORMATION: primer

<400> SEQUENCE: 47
gctcggtctt aagcaaat 18

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gcatcgtcaa ccatttaaag 20

<210> SEQ ID NO 49
<211> LENGTH: 18
<212> TYPE: DNA
<213> ORGANISM: Artificial Sequence
<220> FEATURE:
<223> OTHER INFORMATION: primer

<400> SEQUENCE: 49
ctcagcttga aatgcatc 18

<210> SEQ ID NO 50
<211> LENGTH: 18
<212> TYPE: DNA
<213> ORGANISM: Artificial Sequence
<220> FEATURE:
<223> OTHER INFORMATION: primer

<400> SEQUENCE: 50
gctgcacgtt tactgtat 18

<210> SEQ ID NO 51
<211> LENGTH: 18
<212> TYPE: DNA
<213> ORGANISM: Artificial Sequence
<220> FEATURE:
<223> OTHER INFORMATION: primer -continued

```
<400> SEQUENCE: 51

ctcagcttga aatgcatc                                                    18


<210> SEQ ID NO 52
<211> LENGTH: 18
<212> TYPE: DNA
<213> ORGANISM: Artificial Sequence
<220> FEATURE:
<223> OTHER INFORMATION: primer

<400> SEQUENCE: 52

gctgcacgtt tactgtat                                                    18


<210> SEQ ID NO 53
<211> LENGTH: 18
<212> TYPE: DNA
<213> ORGANISM: Artificial Sequence
<220> FEATURE:
<223> OTHER INFORMATION: primer

<400> SEQUENCE: 53

cttagatttc actgctgc                                                    18
```

RECOMBINANT ACID-RESISTANT YEAST WITH SUPPRESSED GLYCEROL PRODUCTION AND METHOD OF PRODUCING LACTIC ACID USING THE SAME

CROSS REFERENCE TO RELATED APPLICATION

This application claims priority to KR patent application No. 10-2020-0046779, filed Apr. 17, 2020, the contents of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 31, 2021, is named 217079_PF-B2547_ST25.txt, and is 57,812 bytes in size.

BACKGROUND OF THE INVENTION

Field of the Invention

The present invention relates to a recombinant acid-resistant yeast having lactic acid-producing ability and suppressed glycerol production and a method of preparing lactic acid using the same. More particularly, the present invention relates to a recombinant acid-resistant yeast into which a gene involved in lactic acid production is introduced and in which a gene involved in glycerol production is deleted or attenuated, and a method of preparing lactic acid using the same.

Description of the Related Art

Polylactic acid (PLA) is a biodegradable polymer that is prepared by converting lactic acid into lactide and conducting ring-opening polymerization thereon. The raw material thereof, lactic acid, is produced through fermentation. PLA is widely used in disposable food containers, and has an advantage in that it is capable of being used alone or in the form of a composition or a copolymer in plastics for a variety of industries including the automobile and fiber industries. In addition, it is a representative polymer that has come to be used in 3D printing in recent years, and is an eco-friendly polymer that generates lower amounts of harmful gases and odors when used for 3D printers.

A traditional lactic acid production process is performed using lactic acid bacteria, and includes conducting fermentation while maintaining a neutral pH of 6 to 8 using various forms of Ca salt/Ma salt or a neutralizing agent such as ammonia in order to prevent bacterial death or slowing of growth thereof due to lactic acid produced and accumulated by lactic acid bacteria. When fermentation is completed, microorganisms are separated, and sulfuric acid is added to convert lactate to lactic acid while Ca salt is removed in the form of $CaSO_4$ due to the difficulty of separation of salt from water and conversion thereof to lactide. In this process, $CaSO_4$, a byproduct, is produced in an amount greater than the amount of lactic acid, thus deteriorating process efficiency.

In general, PLA produces lactic acid through fermentation, and then converts the produced lactic acid into lactide through a purification process. For conversion to lactide, a process of converting lactic acid into a hydrogenated form is required, and the pH for neutral fermentation is generally 6 to 7, and the neutral pH is thus changed to an acidic pH using a large amount of sulfuric acid. In this process, a large amount of neutralization salts is generated, and economic feasibility is deteriorated due to the low value of the neutralization salts along with the cost of investing in processes to remove the neutralization salts.

Meanwhile, lactic acid has L- and D-type optical isomers. There are a variety of microbial populations. For example, lactic acid bacteria that mainly produce L-type optical isomers often also produce about 5-10% D-type optical isomers, and strains that mainly produce D-type optical isomers include strains that produce both D-type and L-type optical isomers, strains that produce both D-type optical isomers and ethanol, and the like (Ellen I. *Garvie, Microbiological Reviews,* 106-139, 1980).

Meanwhile, in the case of *Lactobacillus*, which produces lactic acid in nature, a large amount of expensive nutrients must be used as a medium in order to commercially produce lactic acid. This excess of nutrient components greatly inhibits a downstream polymerization process or a lactide conversion process, or in the case in which lactide is used as an intermediate, costs for purification processes such as adsorption, distillation and ion exchange are incurred in order to obtain high-yield and high-purity polymers or precursors thereof, thus further increasing production costs. Research on the use of yeast has been suggested in order to solve these problems. Yeast is known to conduct growth/fermentation even when inexpensive nutrients are used, and to be highly resistant to acidic conditions.

When lactic acid is produced using yeast that grows well in acid (hereinafter referred to as "acid-resistant yeast"), it is not necessary to maintain the medium at a pH of 6 to 7 using a neutralizing agent during fermentation, so the fermentation process is simplified and a downstream purification process for removing the neutralizing agent is not required. In addition, yeast itself produces many components that it requires for metabolism, and thus can be cultured in a medium with a relatively low nutrient level compared to bacteria, particularly *Lactobacillus*, thus obviating downstream purification processes and significantly lowering production costs.

However, there is a requirement for technology for producing lactic acid using yeast. The requirement is that the yield, productivity, and concentration of lactic acid, which are indicators for strain fermentation performance, must be maintained at high levels similar to the performance of lactic acid bacteria in order for the technology to be commercially applied.

Although acid-resistant lactic acid technology using yeast has been developed, in practice, in many cases, high-performance fermentation capability is obtained only when fermentation is performed while maintaining a pH of at least 3.7, which is not less than the pKa value of lactic acid, by performing a neutralization reaction during the fermentation. For this reason, it is not reasonable to determine that the technology is a practical method for achieving acid resistance, and it is difficult to anticipate an effect of reducing production costs when applied to a process (Michael Sauer et al., *Biotechnology and Genetic Engineering Reviews,* 27:229-256, 2010).

Therefore, acid-resistant yeasts capable of reducing processing costs can be commercially applied only when they are capable of completing fermentation at a pH of a fermentation solution not more than the pKa value, without using a neutralizing agent or using the same in a minimum amount, and three major fermentation indicators achieve levels similar to those for lactic acid bacteria.

In general, yeast metabolizes ethanol as a main product, produces glucose as a byproduct, and produces hardly any lactic acid. In addition, since the probability of selecting a strain that produces lactic acid from microorganisms having high acid resistance is very low, the present inventors selected a yeast strain having excellent acid resistance, and attempted to construct a strain that is imparted with lactic acid-producing ability and has suppressed ethanol- and glycerol-producing ability from the selected strain through a genetic engineering method.

Accordingly, as a result of intensive efforts to produce an acid-resistant strain with lactic acid-producing ability and suppressed glycerol-producing ability, the present inventors have constructed a recombinant strain by removing a gene involved in glycerol production from an acid-resistant yeast and further introducing a gene encoding lactate dehydrogenase into the yeast, and found that the amount of glycerol, which acts as an impurity in lactic acid production using the recombinant yeast, decreased when lactic acid was produced using the recombinant strain. Based on this finding, the present invention was completed.

SUMMARY OF THE INVENTION

Therefore, the present invention has been made in view of the above problems, and it is one object of the present invention to provide a recombinant acid-resistant yeast strain having lactic acid-producing ability and suppressed glycerol-producing ability.

It is another object of the present invention to provide a method of preparing lactic acid using the recombinant acid-resistant yeast strain.

It is another object of the present invention to provide a gene encoding an enzyme that converts dihydroxyacetone phosphate into glycerol-3-phosphate derived from the acid-resistant yeast.

In accordance with one aspect of the present invention, the above and other objects can be accomplished by the provision of a recombinant strain having lactic acid-producing ability, in which a gene encoding an enzyme that converts dihydroxyacetone phosphate to glycerol-3-phosphate is deleted or attenuated from an acid-resistant yeast YBC strain (KCTC13508BP) and a gene encoding lactate dehydrogenase is introduced into the acid-resistant yeast YBC strain.

In accordance with another aspect of the present invention, there is provided a recombinant strain having lactic acid-producing ability, in which a GPD1 gene, which is a gene encoding an enzyme that converts dihydroxyacetone phosphate to glycerol-3-phosphate;

a CYB2 gene, which is a gene encoding an enzyme that converts lactate into pyruvate;

an ADH gene, which is a gene encoding alcohol dehydrogenase, and a PDC gene, which is a gene encoding pyruvate decarboxylase is deleted from an acid-resistant yeast YBC strain (KCTC13508BP); and in which a gene encoding lactate dehydrogenase is introduced into the acid-resistant yeast YBC strain.

In accordance with another aspect of the present invention, there is provided a method for producing lactic acid including: (a) culturing the recombinant strain to produce lactic acid; and (b) collecting the produced lactic acid.

In accordance with another aspect of the present invention, there is provided a gene having enzymatic activity of converting hydroxyacetone phosphate to glycerol-3-phosphate, the gene encoding a protein having a homology of 90% or more with a protein comprising the amino acid sequence of SEQ ID NO: 3.

In accordance with another aspect of the present invention, there is provided a protein having enzymatic activity of converting dihydroxyacetone phosphate to glycerol-3-phosphate, the protein having a homology of 90% or more with a protein comprising the amino acid sequence of SEQ ID NO: 3.

In accordance with another aspect of the present invention, there is provided a promoter of a GPD1 gene comprising the nucleotide sequence of SEQ ID NO: 4 or SEQ ID NO: 5.

Effects of the Invention

When producing lactic acid using the recombinant acid-resistant yeast according to the present invention, the production of lactic acid is maintained while the production of glycerol is reduced, so that crosslinking by glycerol can be suppressed in the oligomerization reaction for conversion to lactide and thus the conversion yield of lactic acid to lactide can be increased.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
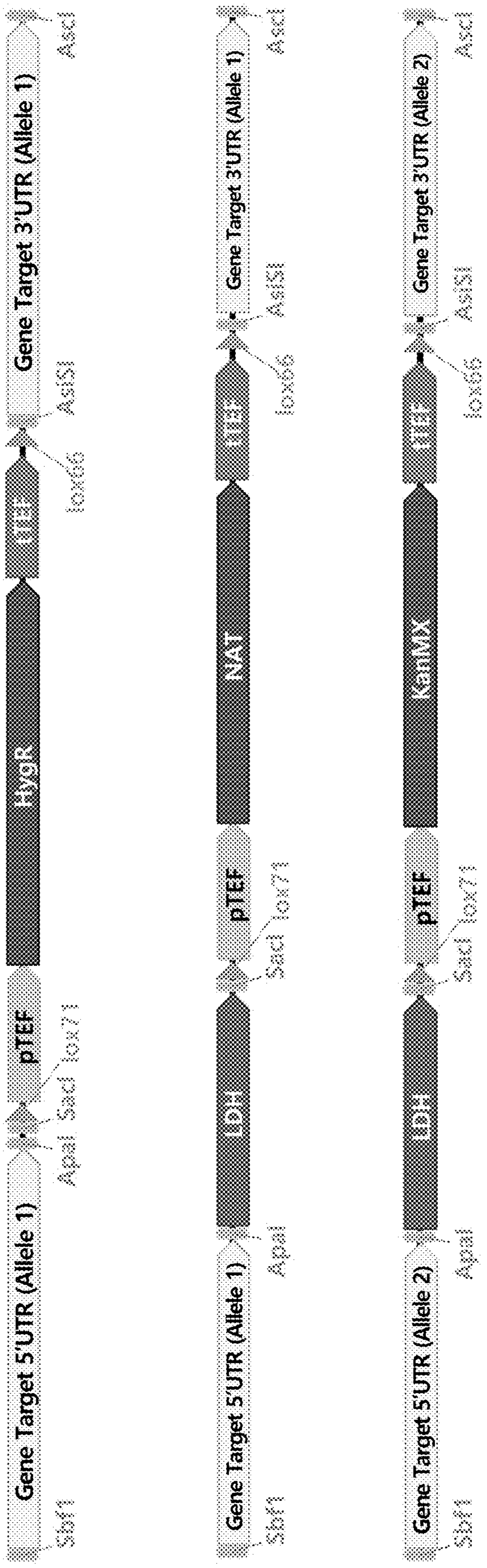
FIG. 1 shows an example of a deletion cassette used to delete the GPD1(g1544)/GPD2(g5617) genes from the genome of the YBC4 strain in the present invention, or to delete the genes and insert the LDH gene instead thereof.
Figure 2:
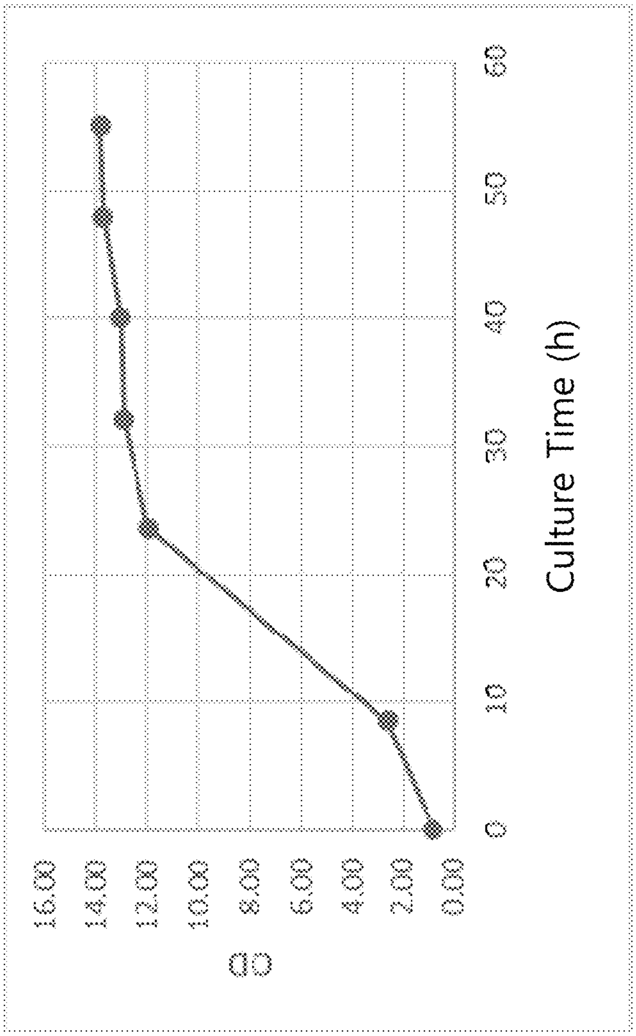
FIGS. 2, 3, 4 and 5 show a fermentation profile of the recombinant yeast strain, YBC5 strain according to the present invention.
Figure 3:
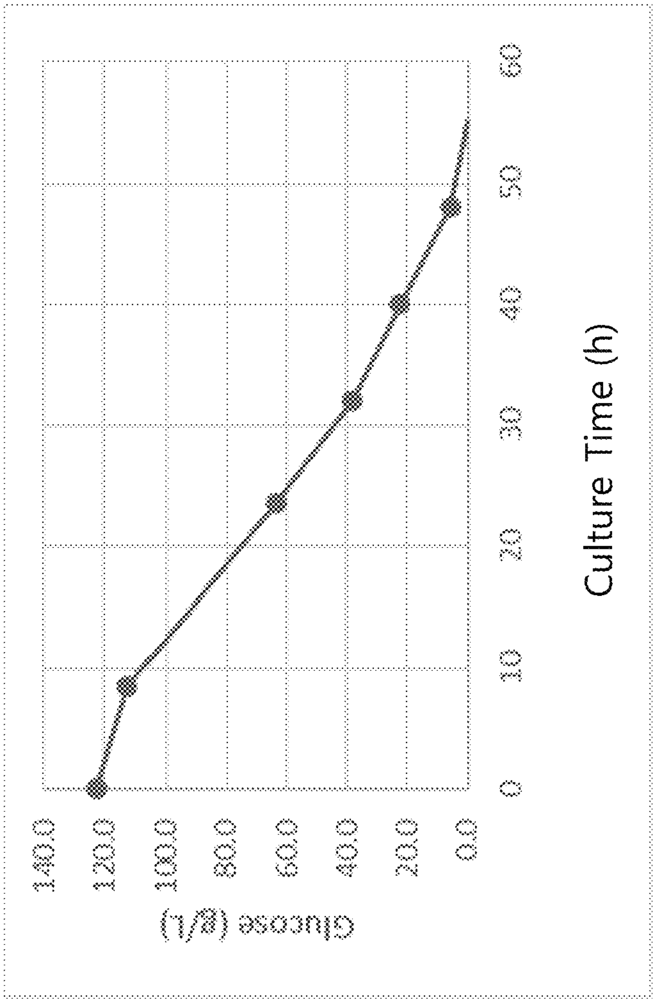
Figure 4:
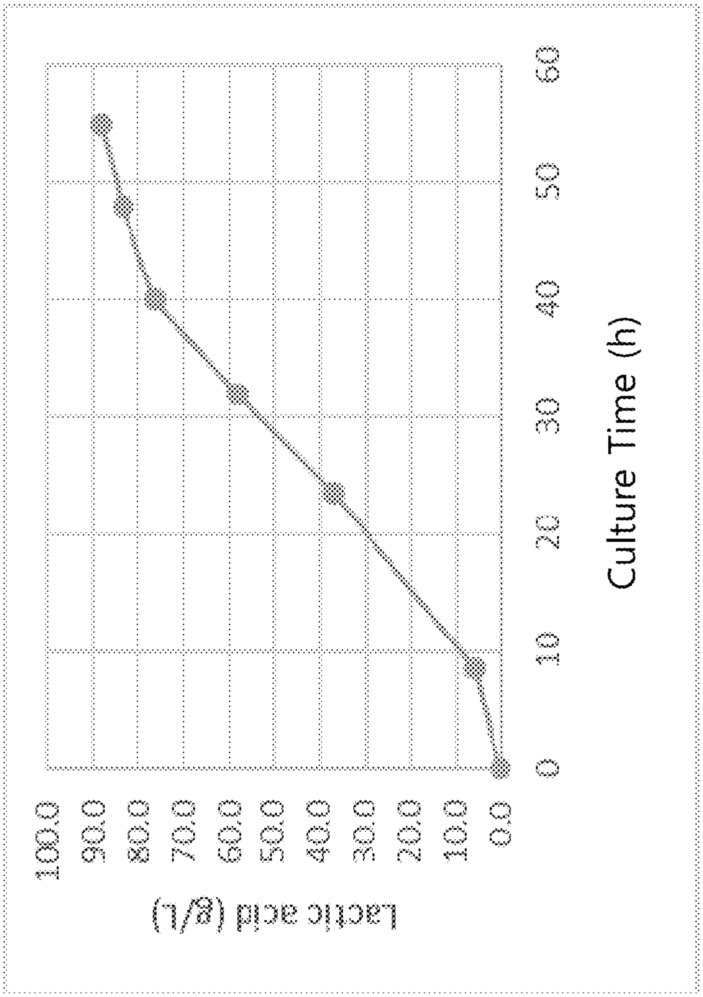
Figure 5:
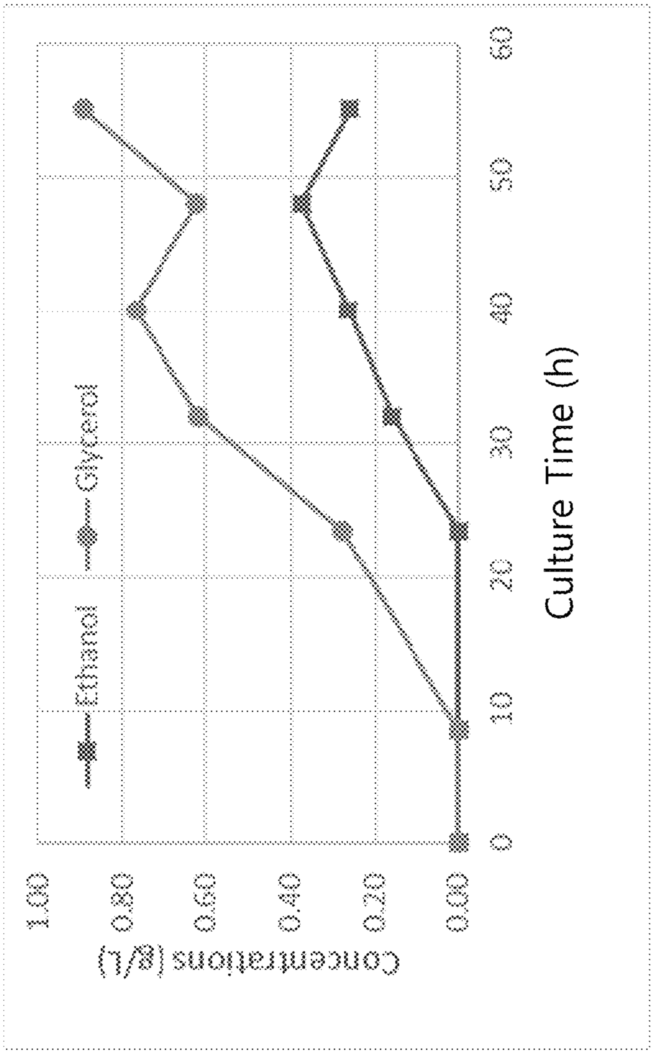

Unless defined otherwise, all technical and scientific terms used herein have the same meanings as appreciated by those skilled in the field to which the present invention pertains. In general, the nomenclature used herein is well-known in the art and is ordinarily used.

Acid-resistant yeast is characterized by consuming sugar at a high rate even at an acidic pH, exhibiting a high growth rate, and converting the consumed sugar into a desired product under fermentation conditions. In the previous research by the present inventors, an acid-resistant yeast strain (KCTC13508BP) was selected from yeasts having these characteristics in several yeast libraries, and the acid-resistant yeast strain (KCTC13508BP) had a high growth rate and a high sugar consumption rate even at a lactic acid concentration of 40 g/L to 80 g/L. By controlling the metabolic circuit to improve the lactic acid-producing ability and suppress the ethanol-producing ability of the acid-resistant yeast YBC strain, a recombinant strain was produced by deleting a gene encoding the cytochrome b2 enzyme that converts lactate to pyruvate from the strain, which is obtained by deleting a gene encoding alcohol dehydrogenase and a gene encoding pyruvate decarboxylase from the YBC strain and introducing a lactate dehydrogenase gene into the YBC strain. In addition, in order to suppress glycerol production in the constructed strain, a recombinant strain was constructed by deleting a gene encoding a glycerol-3-phosphate dehydrogenase that converts hydroxyacetone phosphate to glycerol 3-phosphate from the strain, and the recombinant strain was found to have improved lactic-acid-producing ability and suppressed ethanol-producing ability and glycerol-producing ability.

In addition, the excess carbon due to the reduced glycerol may be distributed to other byproducts. However, there is a potential to further increase the yield of lactic acid production when converted to lactic acid (for example, enhancement of lactate dehydrogenase).

Therefore, in one aspect, the present invention is directed to a recombinant strain having lactic acid-producing ability, in which a gene encoding an enzyme that converts dihydroxyacetone phosphate to glycerol-3-phosphate is deleted or attenuated from an acid-resistant yeast YBC strain (KCTC13508BP) and a gene encoding lactate dehydrogenase is introduced into the acid-resistant yeast YBC strain.

In general, glycerol is a major byproduct of yeast, and functions to balance the redox in the cells, more particularly, to regulate the balance of NAD/NADH inside the cells that occurs during the production of ethanol or lactate, and to suppress water loss in the cells due to osmotic pressure that occurs when the activity decreases, and also functions as a precursor of glycerol 3-phosphate, which is a precursor of triglyceride, a major energy storage (Roeland Costenoble et al., *Yeast* 16: 1483-1495,2000; Elke Nevoigt and Ulf Stahl, *FEMS Microbiology Reviews* 21:231, 1997).

Known methods for suppressing the glycerol production reaction in yeast include removing or attenuating genes directly relating to glycerol production, and modifying genes relating to a regulatory mechanism such as osmotic pressure. There is a HOG (high-osmolarity glycerol) signaling pathway for the regulatory mechanism such as osmotic pressure (Joseph P Dexter et al., *BMC Systems Biology,* 9:17,2015), and glycerol production is suppressed by removal or modification of the related major factor, SSK1 (cytoplasmic phosphorelay intermediate osmosensor and regulator) or the like (Hubmann et al., *Biotechnology for Biofuels,* 6:87, 2013, Hubmann et al., *Metabolic Engineering,* 17:68, 2013).

However, a great deal of research is required for the regulation of these signaling pathways through mutations, and verification for each step is requires for a certain strain such as the acid-resistant yeast YBC strain (KCTC13508BP). Thus, a more general method, namely, a method of removing the genes directly relating to GPD (NAD-dependent glycerol-3-phosphate dehydrogenase) and GPP (DL-glycerol-3-phosphate phosphatase) was used. GPD1 mainly functions to regulate the osmotic resistance of yeast, and GPD2, which is an isoform of GPD1, is expressed in *S. cerevisiae* to regulate cell activity under anaerobic conditions. In addition, two GPP genes for converting glycerol-3-phosphate to glycerol in *S. cerevisiae* are well known. GPP1 is expressed under anaerobic conditions whereas GPP2 is expressed by osmotic pressure. When each isomer of GPD and GPP is removed, the effect of each case on glycerol production differs depending on the culture conditions and the corresponding strain (Roeland Costenoble et al., *Yeast* 16:1483, 2000; Jacobus Albertyn et al., *Molecular and cellular biology,* 4135, 1994). For this reason, the best method has been considered to be detection of the effect of each case using experimentation.

According to the present invention, the gene encoding an enzyme that converts dihydroxyacetone phosphate to glycerol-3-phosphate may be a GPD1 or GPD2 gene, and preferably, the gene encoding an enzyme that converts dihydroxyacetone phosphate to glycerol-3-phosphate is a GPD1 (g1544) gene, wherein the gene may comprise the nucleotide sequence of SEQ ID NO: 1 or SEQ ID NO: 2.

In one embodiment of the present invention, the g4423 gene as a main ADH gene was removed from the YBC strain, the LDH gene of SEQ ID NO: 12 derived from *Lactobacillus plantarum* was introduced at the position of the g4423 gene, the g3002 gene (hereinafter, referred to "g3002-1 gene") as the CYB2 gene was removed therefrom and the LDH gene was introduced at the position of the g3002-1 gene, to construct a recombinant strain YBC2. The g2947 gene was removed from the recombinant strain YBC2 and the LDH gene was introduced thereinto to construct a recombinant strain YBC4. The g1544 gene as the GPD1 gene was removed from the recombinant strain YBC4 to construct a recombinant strain YBC5. The recombinant strains were cultured and it was confirmed that the improved lactic acid-producing ability, the suppressed ethanol-producing ability and the glycerol-producing ability of the strains were detected.

According to the present invention, the recombinant strain may be characterized in that the gene encoding alcohol dehydrogenase (ADH gene) is further deleted, the gene encoding alcohol dehydrogenase is a g4423 gene and the g4423 gene comprises the sequence of SEQ ID NO: 6 or SEQ ID NO: 7.

According to the present invention, the recombinant strain may be characterized in that an LDH gene is further introduced instead of the ADH gene.

According to the present invention, the recombinant strain may be characterized in that the gene encoding pyruvate decarboxylase (PDC gene) is further deleted, the gene encoding pyruvate decarboxylase is a g3002 gene, and the g3002 gene comprises the sequence of SEQ ID NO: 8 or SEQ ID NO: 9.

According to the present invention, the recombinant strain may be characterized in that an LDH gene is further introduced instead of the PDC gene.

According to the present invention, the recombinant strain may be characterized in that a cytochrome b2 gene (CYB2 gene) that converts lactate to pyruvate is further deleted, the gene encoding cytochrome b2 gene is a g2947 gene and the g2947 gene comprises the sequence of SEQ ID NO: 10 or SEQ ID NO: 11.

According to the present invention, the recombinant strain may be characterized in that an LDH gene is further introduced instead of the CYB2 gene.

According to the present invention, the recombinant strain may be characterized in that an LDH gene is further introduced instead of the GPD1 gene.

According to the present invention, the YBC5 strain has reduced or suppressed glycerol-producing ability than the parent strain, namely, YBC strain (KCTC13508BP) and the mutant strains YBC1/YBC2/YBC3/YBC4 strains derived from the parent strain through deletion or attenuation of the g1544 gene.

According to the present invention, the gene encoding lactate dehydrogenase that is introduced is preferably an LDH gene derived from *L. helveticus*, an LDH gene derived from *R. oryzae*, or an LDH gene derived from *L. plantarum*, more preferably an LDH gene derived from *L. plantarum.*

In another aspect, the present invention is a recombinant strain having lactic acid-producing ability, in which a GPD1 gene, which is a gene encoding an enzyme that converts dihydroxyacetone phosphate to glycerol-3-phosphate; a CYB2 gene, which is a gene encoding an enzyme that converts lactate into pyruvate; an ADH gene, which is a gene encoding alcohol dehydrogenase, and a PDC gene, which is a gene encoding pyruvate decarboxylase is deleted from an acid-resistant yeast YBC strain (KCTC13508BP); and in which a gene encoding lactate dehydrogenase is introduced into the acid-resistant yeast YBC strain.

According to the present invention, the gene encoding lactate dehydrogenase is introduced at the position of at least one of the deleted CYB2 gene, ADH gene, PDC gene and GPD1 gene and is regulated by the promoter of the deleted and substituted gene.

In one embodiment of the present invention, the YBC5 strain (Δg4423::ldh/Δg3002-1::ldh/Δg2947::ldh/Δg1544) exhibits greatly reduced glycerol-producing ability compared to the YBC4 strain (Δg4423::ldh/Δg3002-1::ldh/Δg2947::ldh). Although glycerol was not completely removed, this is rather advantageous in terms of environmental adaptation of the strain. In other words, strains that completely lose glycerol-producing ability lose the ability thereof to adapt to stress environments such as external osmotic pressure, which is the original function thereof, and become very attenuated. These strains cannot endure stress such as general commercial scale pressure, salt concentration and product inhibition and thus fail to conduct fermentation normally. Therefore, the strain of the present invention exhibits very excellent performance to achieve the desired glycerol reduction without causing adverse effects.

Accordingly, in another aspect, the present invention is directed to a method of producing lactic acid including (a) culturing the recombinant strain to produce lactic acid, and (b) collecting the produced lactic acid.

According to the present invention, an excellent acid-resistant strain having greatly increased lactate production, greatly reduced ethanol production and greatly reduced glycerol byproducts could be expected.

In another aspect, the present invention is directed to a gene having enzymatic activity of converting hydroxyacetone phosphate to glycerol-3-phosphate, the gene encoding a protein having a homology of 90% or more with a protein comprising the amino acid sequence of SEQ ID NO: 3.

According to the present invention, the gene has enzymatic activity for converting hydroxyacetone phosphate to glycerol-3-phosphate, and encodes a protein having a homology of 90% or more, preferably 95% or more, even more preferably, 98% or more, and still more preferably 99% or more with the protein comprising the amino acid sequence of SEQ ID NO: 3.

In the present invention, the gene may comprise a nucleotide sequence of SEQ ID NO: 1 or SEQ ID NO: 2.

In another aspect, the present invention is directed to a protein having enzymatic activity of converting dihydroxyacetone phosphate to glycerol-3-phosphate, the protein having a homology of 90% or more with a protein comprising the amino acid sequence of SEQ ID NO: 3.

In the present invention, the protein has an enzymatic activity for converting dihydroxyacetone phosphate to glycerol-3-phosphate, and encodes a protein having a homology of 90% or more, preferably 95% or more, even more preferably, 98% or more, and still more preferably 99% or more with the protein comprising the amino acid sequence of SEQ ID NO: 3.

In another aspect, the present invention is directed to a promoter of a GPD1 gene comprising the nucleotide sequence of SEQ ID NO: 4 or SEQ ID NO: 5.

As used herein, the term "acid-resistant yeast" is defined as a yeast that can maintain a biomass consumption rate (such as a sugar consumption rate) of at least 10% or a specific growth rate of at least 10%, at a pH less than a pKa value of an organic acid when the medium contains an organic acid (particularly lactic acid) at a concentration of at least 1M, compared to when the medium does not contain an organic acid. More specifically, the term "acid-resistant yeast" is defined as yeast that can maintain a biomass consumption rate (such as a sugar consumption rate) of at least 10% or a specific growth rate of at least 10% at a pH of 2 to 4 compared to a pH of 5 or higher.

The recombinant yeast according to the present invention can be produced by inserting the gene into a chromosome of a host yeast according to a conventional method, or by introducing a vector including the gene into the host yeast.

As the host yeast, a host cell having high DNA introduction efficiency and high expression efficiency of the introduced DNA is commonly used. In one embodiment of the present invention, an acid-resistant yeast is used, but the present invention is not limited thereto and any type of yeast may be used as long as it can sufficiently express the target DNA.

The recombinant yeast can be prepared according to any transformation method. The term "transformation" refers to a phenomenon in which DNA is introduced into a host to enable DNA to be replicated as a factor of chromosomes or by chromosomal integration, and means a phenomenon in which genetic changes are artificially induced by introducing external DNA into a cell. General transformation methods include electroporation, lithium acetate-PEG, and the like.

In addition, in the present invention, any commonly known genetically engineering method can be used as a method of inserting genes into the chromosomes of host microorganisms. For example, there are methods using retroviral vectors, adenoviral vectors, adeno-associated virus vectors, herpes simplex viral vectors, pox viral vectors, lentiviral vectors, non-viral vectors and the like. The "vector" means a DNA product containing a DNA sequence operably linked to a suitable regulatory sequence capable of expressing the DNA in a suitable host. Vectors may be plasmids, phage particles or simply potential genomic inserts. When transformed into a suitable host, vectors may be replicated or perform functions independent of the host genomes, or some thereof may be integrated with the genomes. Plasmids are currently the most commonly used forms of vector, but linear DNA is also a commonly used form for genomic integration of yeast.

Typical plasmid vectors include (a) a replication origin to efficiently conduct replication so as to include a predetermined amount of plasmid vector in each host cell, (b) an antibiotic resistance gene or auxotrophic marker gene to screen host cells transformed with plasmid vectors, and (c) a restriction enzyme cleavage site into which a foreign DNA fragment is inserted. Even if an appropriate restriction enzyme cleavage site is not present, the vector and foreign DNA can be easily ligated using a synthetic oligonucleotide adaptor or a linker according to a conventional method (Gibson assembly). If necessary, a method of synthesizing and using the entire desired sequence is also commonly used.

Furthermore, when a nucleic acid sequence is aligned with another nucleic acid sequence based on a functional relationship therebetween, it is said to be "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide when expressed as a pre-protein involved in the secretion of the polypeptide; a promoter or enhancer is operably linked to a coding sequence when it affects the transcription of the sequence; a ribosome-binding site is operably linked to a coding sequence when it affects the transcription of the sequence; or the ribosome-binding site is operably linked to a coding sequence when positioned to facilitate translation.

Generally, the term "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adaptor or a linker according to a conventional method is used.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of times the vector replicates, the ability to control the number of times the vector replicates, and the expression of other proteins encoded by the corresponding vector, such as the expression of antibiotic markers, should also be considered.

In the present invention, the carbon source may include, but is not limited to, one or more selected from the group consisting of glucose, xylose, arabinose, sucrose, fructose, cellulose, galactose, glucose oligomer, and glycerol.

In the present invention, the culture may be performed under conditions such that microorganisms, for example, *E. coli*, and the like no longer act (for example, cannot produce metabolites). For example, the culture may be carried out at a pH of 1.0 to 6.5, preferably a pH of 1.0 to 6.0, and more preferably a pH of 2.6 to 4.0, but is not limited thereto.

Hereinafter, the present invention will be described in more detail with reference to examples. However, it will be obvious to those skilled in the art that these examples are provided only for illustration of the present invention and should not be construed as limiting the scope of the present invention.

Example 1: Analysis of Glycerol-Producing Gene in Genome of Acid-Resistant Strain YBC The present inventors selected strains having acid resistance through testing on various yeast strains and determined the strain having the best acid resistance, namely, the YBC strain, by adding lactic acid to a medium at the beginning of the culture of yeast strains and monitoring the growth and sugar consumption rate of microorganisms, and deposited the strain with accession number KCTC13508BP with the Biological Resource Center in the Korea Research Institute of Bioscience and Biotechnology.

Phylogenetic analysis showed that the YBC strain (KCTC13508BP) is a strain similar to *S. cerevisiae*, is diploid, and is Crabtree-positive.

g1544 and g5617 were identified as the genes annotated with GPD1 (glycerol-3-phosphate dehydrogenase 1) and GPD2, respectively, which are genes encoding an enzyme that converts dihydroxyacetone phosphate present in the genome of the YBC strain to glycerol-3-phosphate using *S. cerevisiae* and bioinformatics information from the whole-genome sequence data of the YBC strain. Two GPP genes encoding an enzyme that converts glycerol 3-phosphate to glycerol were identified, namely g4356 and g5443, having very similar homology in the genome of the YBC strain, and with current information, it is difficult to discern the functions of two genes based on GPP1 and GPP2. Thus, these genes are called "GPP1 v.1" and "GPP1 v.2".

Table 1 compares the similarity in the amino acid sequences of GPD1 and GPD2 of YBC and *Saccharomyces cerevisiae*.

TABLE 1

Comparison of protein sequence homology of GPD1 and GPD2 of YBC and *S. cerevisiae* strains

| | YBC GPD1 | YBC GPD2 | Sc GPD1 | Sc GPD2 |
|---|---|---|---|---|
| YBC GPD1 | 100 | 69.78 | 78.06 | 63.49 |
| YBC GPD2 | 69.78 | 100 | 71.25 | 63.60 |
| *S. cerevisiae* GPD1 | 78.06 | 71.25 | 100 | 65.08 |
| *S. cerevisiae* GPD2 | 63.49 | 63.60 | 65.08 | 100 |

Accordingly, a deletion cassette capable of removing the GPD1 gene (g1544 gene) (SEQ ID NO: 1 and SEQ ID NO: 2) and the protein thereof (SEQ ID NO: 3) was constructed, a deletion cassette capable of removing the GPD2 gene (g5617 gene) (SEQ ID NO: 13 and SEQ ID NO: 14) and the protein thereof (SEQ ID NO: 15) was constructed, and a deletion cassette capable of removing the GPP1 gene (v.1; g4356 gene) (SEQ ID NO: 16 and SEQ ID NO: 17), the GPP1 gene (v.2; g5443 gene) (SEQ ID NO: 19 and SEQ ID NO: 20), and the proteins thereof (SEQ ID NO: 18 and SEQ ID NO: 21) was constructed.

The deletion cassette used herein is shown in FIG. 1, and methods of selecting a corresponding restriction enzyme site or an antibiotic resistance gene and removing the antibiotic resistance gene are well known in the related art, and may be used with various modifications.

In general, when GPD1 and GPD2, or GPP1 and GPP2, among the genes producing glycerol, are simultaneously removed, the ability of the strain to grow and adapt to the external environment is completely blocked, and thus the strain is very sensitive to osmotic pressure or the like and is inappropriate for fermentation, which is well-known in the art. Therefore, when glycerol reduction was found to be insufficient after removing GPD1 or GPD2, GPP1 v1 or GPP1 v2 was further removed from each GPD1/2-removed strain as a strategy to increase glycerol reduction.

Example 2: Measurement of Expression Level of GPD Gene

In order to confirm the expression levels of GPD1 (g1544) and GPD2 (g5617) of the YBC strain, RT-qPCR was performed using the following primers and the ALG9 gene as a housekeeping gene. The RT-qPCR method used in this example will be described as follows. RNA was extracted during the logarithmic growth phase of the YBC strain, and cDNA was produced using the RNA as a template. Primers specific to each of the target genes (GPD 1 and GPD2) and housekeeping genes (used as Ref genes) were synthesized and used to conduct qPCR. The Ref gene used in the experiment was ALG9, and the size of the fragment amplified by the primer that was used is 147f 3 bp.

ALG9 forward primer:
(SEQ ID NO: 22)
CTTTGAGTGCAAGTATCGCC

ALG9 reverse primer:
(SEQ ID NO: 23)
TGTGTAATTGTTCACCAAAGCC

GPD1(g1544) forward primer:
(SEQ ID NO: 24)
GTCGATTCTCATGTTCGTGC

GPD1 reverse primer:
(SEQ ID NO: 25)
CTTAGCGACTTCAGTAGCGA

GPD2(g5617) forward primer:
(SEQ ID NO: 26)
CATGTATCGAATCAAGTTCGTG

GPD2 reverse primer:
(SEQ ID NO: 27)
CAACTTCTGGTGCTAAATTTGC

Regarding the expression level of the gene in the YBC strain, the YBC strain exhibited a GPD1 expression rate of about 20 times that of ALG9 after 14 hours of culture and about 70 times of that of ALG9 after 23 hours of culture, and the YBC strain exhibited a very low GPD2 expression rate, similar to that of ALG9.

The results described above tentatively suggest that GPD1 plays a major role as an enzyme that converts dihydroxyacetone phosphate to glycerol-3-phosphate in the YBC strain. In order to verify the actual role, a strain from which each gene has been removed was constructed.

Example 3: Construction of Recombinant Acid-Resistant Yeast Strain from which GPD Gene is Removed The g1544 gene, the g5617 gene, the g5443 gene and the g4356 gene, annotated with the GPD1 gene, the GPD2 gene, the GPP1 v1 gene and the GPP1 v2 gene, respectively, were removed from the genome of the YBC strain to construct a strain.

The acid-resistant yeast strains used to remove the genes were a YBC1 strain, constructed by introducing an LDH gene into the conventional YBC strain, not the YBC wild-type strain, and deleting an ADH (alcohol dehydrogenase) therefrom, a YBC2 strain capable of producing lactic acid at high efficiency and having suppressed ethanol production, constructed by removing the g3002-1 gene (PDC gene) from the YBC1 strain and introducing LDH thereinto, and a YBC4 strain having removed lactic acid consumption ability, constructed by introducing an LDH gene into the strain and removing g2947, a gene that consumes lactate.

YBC5 was constructed by removing the GPD1 (g1544) gene (removing both allele1 and allele 2, as a diploid strain) from the YBC4 strain, primers in Table 1 below were produced to identify the genotype of the strain, and the genotype of the strain was identified from the genomic DNA of the strain. In addition, at the same time, a strain was constructed by removing the GPD2 (g5617) gene from the YBC5 strain, and the glycerol production ability during fermentation was compared between the produced strains.

The method of constructing the strain is as follows:

The YBC1 strain is a strain obtained by removing the g4423 gene, which is the main ADH gene of the YBC strain, from the YBC strain and introducing the LDH gene of SEQ ID NO: 12 derived from *Lactobacillus plantarum* at the position of g4423. A gene cassette from which the ORF of each gene was removed and which contains 5' and 3' UTR was constructed based on the information of g4423 and UTR thereof and used as donor DNA. For each allele of g4423, the corresponding 5' UTR comprises the sequence of SEQ ID NO: 28 and SEQ ID NO: 29, and the 3' UTR comprises the sequence of SEQ ID NO: 30 and SEQ ID NO: 31. The donor DNA was produced using a cloning method using a restriction enzyme, Gibson assembly, and a method using gene synthesis as described above. The LDH of SEQ ID NO: 12 was synthesized and then introduced at the ORF site of g4423 to produce donor DNA, and the donor DNA was introduced into YBC to construct a recombinant strain YBC1.

In addition, the g3002-1 gene is a gene that is positioned at the scaffold 72 in the genome sequencing of the YBC strain and acts as a PDC gene. The g3002-1 gene (gene positioned at the scaffold 72) was removed from the YBC1 strain and the LDH gene of SEQ ID NO: 12 was introduced thereinto to construct a recombinant strain YBC2.

The cassette for substituting the gene of g3002 was constructed using the corresponding UTR as a recombination site. Similar to the method of introducing LDH into the site of the g4423 gene (ADH) of YBC1 described above, the cassette was constructed using the UTR of g3002-1. However, in order to simplify the process of gene substitution, a donor cassette for one allele was produced without considering allele variation, but it is also possible to produce a donor cassette for each allele. In addition, for the primers used for gene substitution, in addition to the primers used to produce the deletion strain, a pair of primers capable of detecting both LDH and the UTR of g3002-1 were separately used as follows to increase the accuracy of gene substitution.

g3002-1 UTR-LDH-fwd:
(SEQ ID NO: 32)
GCAGGATATCAGTTGTTTG g3002-1 UTR-LDH-rev:
(SEQ ID NO: 33)
AATACCTTGTTGAGCCATAG In addition, the YBC4 strain is a strain constructed by deleting the g2947 gene, which is the main ADH gene of the YBC strain, from the YBC strain and introducing the LDH gene of SEQ ID NO: 13, derived from *Lactobacillus plantarum*, at the position of g2947. The g2947 gene is a gene positioned at scaffold 41 in the genome sequencing of the YBC strain. A gene cassette from which the ORF of each gene was removed and which contains 5' and 3' UTR was constructed based on the information of g2947 and UTR thereof and used as donor DNA. For each allele of g2947, the corresponding 5' UTR comprises the sequence of SEQ ID NO: 34 and SEQ ID NO: 35, and the 3' UTR comprises the sequence of SEQ ID NO: 36 and SEQ ID NO: 37. The donor DNA was produced using a cloning method using a restriction enzyme, Gibson assembly, and a method using gene synthesis as described above.

However, in order to simplify the process of gene substitution, a donor cassette for one allele was produced without considering allele variation, but it is also possible to produce a donor cassette for each allele.

The method of constructing the strain is as follows:

The YBC5 strain is a strain constructed by deleting the g1544 gene, which is the GPD1 gene of the YBC4 strain, from the YBC4 strain. The g1544 gene is a gene positioned at scaffold 19 in the genome sequencing of the YBC strain.

A gene cassette from which the ORF of each gene was removed and which contains 5' and 3' UTR was constructed based on the information of g1544 and UTR thereof and used as donor DNA. For each allele of g1544, the corresponding 5' UTR comprises the sequence of SEQ ID NO: 38 and SEQ ID NO: 39, and the 3' UTR comprises the sequence of SEQ ID NO: 40 and SEQ ID NO: 41. The donor DNA was produced using a cloning method using a restriction enzyme, Gibson assembly, and a method using gene synthesis as described above.

In order to simplify the process of gene substitution, a donor cassette for one allele was produced without considering allele variation, but it is also possible to produce a donor cassette for each allele. In addition, the donor cassette may be produced and applied without using antibiotic markers when a currently commercialized genetic engineering technology (CRISPR) is used.

In addition, for primers used for genotyping after gene substitution, primer pairs that can be used to identify the genotypes of g1544 and g5617 to be described in detail later, as shown in Table 2 below, to increase the accuracy of gene substitution identification.

[Table 2]

Primer set for identifying introduction of g1544 and g5617

| Name | Sequence |
|---|---|
| Primer for detecting G1544 ORF | GGGTACTACTATCGCTAA (SEQ ID NO: 42) CACCGGCAACAGAGATAC (SEQ ID NO: 43) |
| Primer 2nd set for detecting G1544 ORF | CGTACGCAGTGATCCATC (SEQ ID NO: 44) CACCGGCAACAGAGATAC (SEQ ID NO: 45) |
| Primer for detecting G1544 UTR | CGTACGCAGTGATCCATC (SEQ ID NO: 46) GCTCGGTCTTAAGCAAAT (SEQ ID NO: 47) |
| Primer for detecting G5617 ORF | GCATCGTCAACCATTTAAAG (SEQ ID NO: 48) CTCAGCTTGAAATGCATC (SEQ ID NO: 49) |
| Primer 2nd set for detecting G5617 ORF | GCTGCACGTTTACTGTAT (SEQ ID NO: 50) CTCAGCTTGAAATGCATC (SEQ ID NO: 51) |
| Primer for detecting G5617 UTR | GCTGCACGTTTACTGTAT (SEQ ID NO: 52) CTTAGATTTCACTGCTGC (SEQ ID NO: 53) |

The genotypes of the produced recombinant strains are as follows:

YBC2: Δg4423::ldh/Δg3002-1::ldh

YBC4: Δg4423::ldh/Δg3002-1::ldh/Δg2947::ldh

YBC5: Δg4423::ldh/Δg3002-1::ldh/Δg2947::ldh/Δg1544

YBC5a: Δg4423::ldh/Δg3002-1::ldh/Δg2947::ldh/Δg5617

Example 4: Confirmation of Lactic Acid Production Effect and Glycerol Production Inhibitory Effect in Recombinant YBC Strain Constructed by Deleting GPD1 Gene from YBC4 Strain For the recombinant strains YBC5 and YBC5a constructed in Example 3, the inoculation OD was 0.5, and the medium used herein was m-YP medium (5 g/L of peptone, 4 g/L yeast extract, 5 g/L of $KH_2PO_4$, 2 g/L of $MgSO_4$ $7H_2O$, 0.15 g/L of uracil) supplemented with 10% glucose and cultured for 64 hours at 30° C. and 150 rpm in a 500 ml flask.

TABLE 3

Results of culture of YBC4 and YBC5

| | Yield (g/g) | | | |
|---|---|---|---|---|
| | Lactic acid | Ethanol | Glycerol | Acetic acid |
| YBC4 | **0.79** | 0.01 | 0.05 | 0 |
| YBC5 | **0.80** | 0.015 | **0.01** | 0.005 |
| YBC5a | 0.71 | 0.047 | 0.04 | 0.003 |

As a result, as can be seen from Table 3, the YBC5 strain exhibited glycerol-producing inhibition of 80% compared to the YBC4 strain, but produced a small amount of glycerol. As described above, glycerol plays a key role in the adaptation of microorganisms to the environment, particularly to osmotic pressure, and complete glycerol production inhibition through simultaneous removal of GPD1 and GPD2 or simultaneous removal of GPP1 and GPP2 makes the strain extremely sensitive to osmotic pressure and disables normal growth and fermentation of the strain. Thus, the current glycerol reduction rate of YBC5 is considered to be appropriate. However, in this strain, the reduced glycerol did not directly greatly affect the increase in lactic acid production, but the glycerol was distributed among various other byproducts. Thus, the use of a method to increase the yield of lactic acid fermentation in the future is required.

Glycerol may also affect polymerization during the production of PLA, an eco-friendly polymer, and it has been reported that in the presence of glycerol, the structure of PLA changes from a linear form to a branched form due to the structure of glycerol (Wen Shen et al., R. Soc. open sci. 5: 180134, 2018). This change in the structure of PLA may act as an impurity in many subsequent processes, for example, may affect physical properties and formation of a stereo complex PLA by Van der Waals force between L-type PLA and D-type PLA, which have an optical isomer relationship therebetween, and the formation of lactic-acid oligomers for conversion to lactide. Of course, there may be a method of reducing glycerol through a purification process for removing glycerol, but reducing glycerol through genetic engineering as in the present invention is a potent strategy to reduce the incidence of such problems in subsequent processes.

Compared to the YBC5 strain from which GPD1 was removed, the YBC5a strain, from which GPD2 was removed, exhibited somewhat incomprehensible results including almost no glycerol reduction effect, reduced lactic acid production and increased ethanol production. The YBC5a strain, from which GPD2 was removed, was determined to be unsuitable for use as a lactic-acid-producing strain since it inhibited overall lactic acid fermentation.

In the production of the YBC1 to YBC4 strains used to construct the YBC5 strain, the LDH gene was introduced when the main gene was removed, to improve the lactic-acid-producing ability of the strain. However, in the production of the YBC5 strain, the LDH gene was not introduced when the GPD1 gene was removed. The reason for this is that two LDH genes of SEQ ID NO: 12 derived from *Lactobacillus plantarum* were introduced at three positions (6 genes in total), and thus it may be predicted that the introduction of the same gene as above will have a negligible effect of additionally increasing activity in consideration of internal feedback regulation, and the expression rate of GPD1/2 under general conditions is higher than that of the Ref gene, ALG9, as described in Example 2, but is lower than that of ADH or PDC, and the genome may be unstable when a plurality of genes of the same type as each other exists in the genome.

Example 5: Evaluation of Fermentation Performance of YBC5 Strain

In this example, the YBC5 strain was cultured in a bioreactor rather than using a flask culture to confirm the lactic acid fermentation performance thereof.

The YBC5 strain was cultured in mYP medium (5 g/L of peptone, 4 g/L of an yeast extract, 5 g/L of $KH_2PO_4$, 2 g/L of $mgSO_4 \cdot 7H_2O$, and 0.15 g/L of uracil) in 40 ml for $1^{st}$ seed culture and 220 ml for $2^{nd}$ seed culture over 2 days, and then all cells were harvested and inoculated in 2 L mYP medium. The inoculation OD was 0.85, the culture was started in mYP medium supplemented with 12% glucose, and a $CaCO_3$ solution was intermittently injected into the medium to maintain a pH of 3. The culture was conducted at 30° C. and 500 rpm under an air flow of 0.25 vvm.

As a result, as can be seen from FIGS. 2 through 5, the YBC5 strain consumed all glucose within a short time in the bioreactor and produced lactic acid, and at the final pH of 3.3, a lactic acid yield was 0.81 (g/g), productivity was 1.6 g/L/hr, the concentration of the lactic acid that was produced was 88.2 g/L, and a glycerol yield was 0.01 (g/g). This shows that the same result as in Example 3 was obtained in the bioreactor. In addition, it is expected that further improvement of this performance is possible based on the improvement of initial OD and culture conditions in the future.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A recombinant strain having lactic acid-producing ability, wherein the recombinant strain having lactic acid-producing ability is a YBC strain deposited as KCTC13508BP further modified to comprise an introduced gene encoding lactate dehydrogenase and to comprise a deletion or attenuation of a gene encoding an enzyme that converts dihydroxyacetone phosphate to glycerol-3-phosphate.

2. The recombinant strain according to claim 1, wherein the gene encoding the enzyme that converts dihydroxyacetone phosphate to glycerol-3-phosphate is a GPD1 or GPD2 gene.

3. The recombinant strain according to claim 1, wherein the gene encoding the enzyme that converts dihydroxyacetone phosphate to glycerol-3-phosphate is a GPD1 gene, wherein the gene comprises the nucleotide sequence of SEQ ID NO: 1 or SEQ ID NO: 2.

4. The recombinant strain according to claim 1, wherein the recombinant strain is characterized in that a gene encoding alcohol dehydrogenase is further deleted or attenuated.

5. The recombinant strain according to claim 4 wherein the gene encoding alcohol dehydrogenase comprises the sequence of SEQ ID NO: 6 or SEQ ID NO: 7.

6. The recombinant strain according to claim 1, wherein the recombinant strain is characterized in that a gene encoding pyruvate decarboxylase is further deleted or attenuated.

7. The recombinant strain according to claim 6, wherein the gene encoding pyruvate decarboxylase comprises the sequence of SEQ ID NO: 8 or SEQ ID NO: 9.

8. The recombinant strain according to claim 1, wherein the recombinant strain is characterized in that a gene encoding an enzyme that converts lactate to pyruvate is further deleted or attenuated.

9. The recombinant strain according to claim 8, wherein the gene encoding the enzyme that converts lactate to pyruvate comprises the sequence of SEQ ID NO: 10 or SEQ ID NO: 11.

10. A method for producing lactic acid comprising:

(a) culturing the recombinant strain according to claim 1 to produce lactic acid; and (b) collecting the produced lactic acid.

11. A recombinant strain having lactic acid-producing ability, wherein the recombinant strain having lactic acid-producing ability is a YBC strain deposited as KCTC13508BP further modified to comprise an introduced gene encoding lactate dehydrogenase and deletions of:

a GPD1 gene, which is a gene encoding an enzyme that converts dihydroxyacetone phosphate to glycerol-3-phosphate comprising the nucleotide sequence of SEQ ID NO: 1 or SEO ID NO: 2;

a CYB2 gene, which is a gene encoding an enzyme that converts lactate into pyruvate;

an ADH gene, which is a gene encoding alcohol dehydrogenase, and a PDC gene, which is a gene encoding pyruvate decarboxylase.

12. The recombinant strain according to claim 11, wherein the gene encoding lactate dehydrogenase is introduced at a position of at least one of the deleted CYB2 gene, ADH gene, PDC gene and GPD1 gene and is regulated by a promoter of the deleted gene.

* * * * *